United States Patent [19]
Sekiguchi et al.

[11] Patent Number: 5,482,029
[45] Date of Patent: Jan. 9, 1996

[54] VARIABLE FLEXIBILITY ENDOSCOPE SYSTEM

[75] Inventors: Tadashi Sekiguchi, Saitamaken; Hiroshi Fujita, Tochigiken; Megumi Yoshinaga, Tochigiken; Masashi Honda, Tochigiken; Izumi Watanabe, Tochigiken, all of Japan

[73] Assignee: Kabushiki Kaisha Toshiba, Kawasaki, Japan

[21] Appl. No.: 80,630

[22] Filed: Jun. 24, 1993

[30] Foreign Application Priority Data

| Jun. 26, 1992 | [JP] | Japan | 4-168743 |
| Apr. 9, 1993 | [JP] | Japan | 5-083390 |

[51] Int. Cl.6 ............... A61B 1/005; A61B 1/31
[52] U.S. Cl. ............. 600/109; 604/280; 604/281; 600/118; 600/143; 600/146
[58] Field of Search ............ 128/4, 6; 604/95, 604/281, 282; 385/118

[56] References Cited

U.S. PATENT DOCUMENTS

| 4,176,662 | 12/1979 | Frazer | 128/6 |
| 4,601,283 | 7/1986 | Chikama | 128/4 |
| 4,621,618 | 11/1986 | Omagari | 128/6 |
| 4,890,602 | 12/1990 | Hake | 128/4 |
| 4,977,886 | 12/1990 | Takehana et al. | 128/4 |
| 4,977,887 | 12/1990 | Gouda | 128/4 |
| 5,179,935 | 1/1993 | Miyagi | 128/4 |

FOREIGN PATENT DOCUMENTS

| 62-97526 | 5/1987 | Japan . | |
| 62-97526 | 5/1987 | Japan . | |
| 4071524 | 3/1992 | Japan | 128/4 |
| 5-56910 | 3/1993 | Japan . | |
| 5168586 | 7/1993 | Japan | 128/4 |

OTHER PUBLICATIONS

"Shape Memory Alloy Servo Actuator System With Electric Resistance Feedback And Application For Active Endoscope," Proc. of IEEE Inter. Conf. on Robotics and Automation (1988), 427.

*Primary Examiner*—Richard J. Apley
*Assistant Examiner*—John Mulcahy
*Attorney, Agent, or Firm*—Foley & Lardner

[57] ABSTRACT

An endoscope system includes an endoscope section having a flexible pipe insertable into a body cavity. The flexible pipe is divided into a plurality of segments. Each segment has a mechanism, e.g. shape memory alloy, for varying the flexibility of that segment. A main frame unit has a flexibility control section for controlling the flexibility variation mechanisms to correspond to one of a plurality of flexibility control patterns stored in a database.

7 Claims, 38 Drawing Sheets

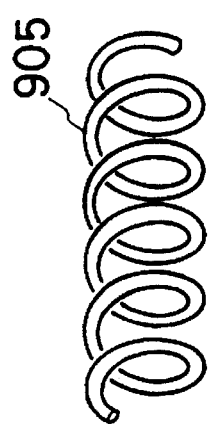
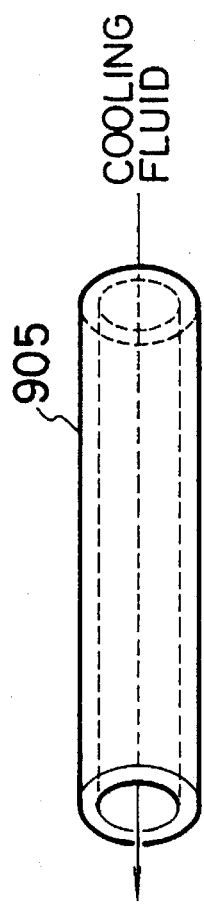
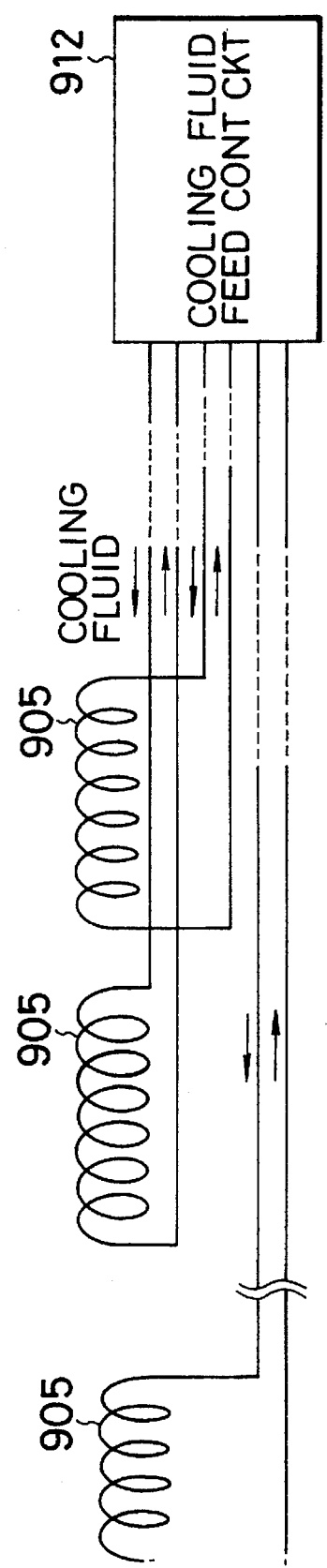

T1: DEFORMATION STARTING TEMPERATURE WITH COMPOSITION 1

T2: DEFORMATION STARTING TEMPERATURE WITH COMPOSITION 2

VARIABLE FLEXIBILITY ENDOSCOPE SYSTEM

BACKGROUND OF THE INVENTION

1. Technical Field

The present invention relates to an endoscope system for diagnosing and remedying disease by inserting an endoscope into a body cavity of a patient, and more specifically to an endoscope system by which the endoscope can be inserted deep into a body cavity without use of any sliding guide pipe.

2. Background Art

In general, an endoscope system or an electronic endoscope system, for instance is roughly composed of a monitor section for displaying endoscope images, a main frame unit provided with various operation switches, and an endoscope section inserted into a body cavity of a patient.

The endoscope section is composed of a flexible pipe and an operation base portion. The flexible pipe is formed into such a structure that a metallic helical pipe is covered with a metallic mesh-shaped braid and further the outer circumference of the mesh-shaped braid is covered with an outer cover. The flexibility of the flexible pipe is determined relatively low near the end thereof (extending from the end to a position about 30 to 40 cm away from the end), but relatively high in the remaining portion. Further, the flexibility of the flexible pipe is regulated by adjusting the pitch of the helical pipe and the elastomer hardness of the outer cover during the manufacturing process.

In the above-mentioned endoscope system, however, when the endoscope is required to be inserted further deep from the curved portion of the E-shaped colon of the large intestine, there exists the case where the endoscope cannot be inserted thereinto. This is because it is impossible to change freely the partial flexibility of the endoscope. To overcome the above-mentioned problem, the curved portion of the S-shaped colon has been so far deformed into a straight line with the use of a guide pipe, so that the endoscope can be inserted being guided along and through the guide pipe.

In the conventional endoscope system as described above, however, since the guide pipe is used before the endoscope is inserted further deep from the curved portion of the S-shaped colon, there exists a danger of occurrence of an accident such that the wall of the intestine is pinched between the endoscope and the guide pipe and thereby injured and bled. Consequently, when the guide pipe is used, it has been so far necessary to watch the fluoroscopic images of the endoscope and the guide pipe taken by an X-ray camera, for instance, thus causing a problem in that the examination is troublesome and further a long diagnosis or remedy time is required.

SUMMARY OF THE INVENTION

With these problems in mind, therefore, it is the object of the present invention to provide an endoscope system by which the endoscope can be easily inserted deep into a body cavity through the curved portion of the S-shaped colon and the traverse colon, without use of any guide pipe.

Further, the other object of the present invention is to provide an endoscope system comprising means for partially changing the flexibility of the flexible pipe of the endoscope. The segments whose flexibility can be changed are easily selected by the operator under remote control in accordance with flexibility patterns obtained when the endoscopes were inserted in the past, thus improving the endoscope insertion and therefore reducing the burden on both the operator and a patient to be examined during the endoscope examination, in particular when the large intestine is diagnosed or remedied.

To achieve the above-mentioned objects, the present invention provides an endoscope system comprising: an endoscope section having a flexible pipe insertable into a body cavity; a monitor section for displaying images obtained by said endoscope as a picture; and a main frame unit having a flexibility control section for controlling flexibility of the flexible pipe for each segment and an image display control section for controlling said monitor section.

In a preferred embodiment of the endoscope system of the present invention, the flexibility of the flexible pipe is controllable for each of a plurality of segments; said main frame unit further comprises a central control section for controlling the flexibility control section and the image display control section, and a data base for storing flexibility rates for each segment of the flexible pipe in the form of a plurality of flexibility control patterns; said monitor section can display at least one flexibility control pattern as a picture; the central control section extracts any flexibility patterns from the data base on the basis of data inputted to the central control section and further displays the extracted patterns on said monitor section; and when any one of the displayed flexibility control patterns is selected, the flexibility control section controls the flexibility of the flexible pipe in accordance with the selected flexibility pattern.

Further, in another preferred embodiment of the present invention, the endoscope system further comprises: an X-ray fluoroscopic apparatus for fluoroscopically observing a body cavity into which the flexible pipe is inserted; and wherein: the flexibility of the flexible pipe can be controlled for each of a plurality of segments; said monitor section can display flexibility rates for each segment of the flexible pipe in the form of a plurality of flexibility control patterns; and when a flexibility rate of each segment is designated, the flexibility control section controls the flexibility of the flexible pipe in accordance with the designated flexibility pattern.

The flexible pipe can be fabricated from a shape memory alloy in the form of a wave-shaped spring.

According to the endoscope system and the flexible pipe of the present invention, since the operator can freely control the flexibility of the flexible pipe during diagnosis with the use of the endoscope, it is possible to provide an optimum flexibility of the flexible pipe. Further, it is possible to allow the endoscope to be easily inserted into a body cavity by controlling the flexibility of the flexible pipe, without causing pain to the patient, thus reducing the diagnosis and remedy time.

Further, when the flexibility of the flexible pipe is controlled on the basis of the X-ray fluoroscopic image information, it is possible to control the flexible pipe more accurately. Furthermore, when the flexibility of the flexible pipe is controlled with the use of a flexibility control data base, it is possible to reduce or eliminate X-rays exposed to the patient.

In the endoscope system according to the present invention, it is possible to eliminate the use of the sliding pipe so far often required for diagnosing the large intestine, thus reducing the unpleasant feeling of the patient during the diagnosis and remedy.

BRIEF DESCRIPTION OF THE DRAWINGS

FIG. 72 is a view showing a tubular memory alloy for cooling the flexible pipe shown in FIG. 69;

FIG. 73 is a view showing the state where the tubular memory alloy shown in FIG. 72 is formed into spiral shape;

FIG. 74 is an illustration showing the state where the shape memory alloy shown in FIG. 73 is provided for each segment of the flexible pipe;

DESCRIPTION OF THE PREFERRED EMBODIMENTS

Embodiments of the endoscope system according to the present invention will be described hereinbelow with reference to the attached drawings.

FIRST EMBODIMENT

Figure 1:
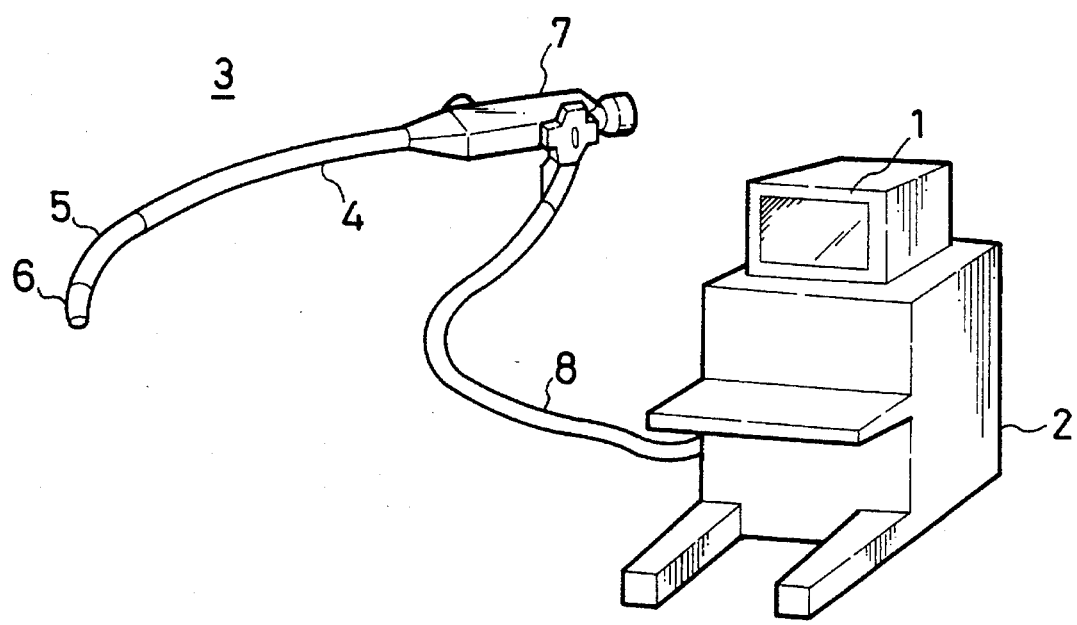
FIG. 1 is a general view showing a first embodiment of the endoscope system according to the present invention.

FIG. 1 is a general view showing the endoscope system of the present invention. The endoscope system comprises a monitor section 1 for displaying endoscope images; a main frame unit 2 provided with operation switches, etc.; and an endoscope section 3 inserted into a body cavity of a patient to be examined.

The endoscope section 3 is composed of an endoscope flexible pipe 4, a curved portion 5, a non-flexible portion 6, an operation section 7, and a universal cord 8.

The curved portion 5 is formed at the end of the endoscope flexible pipe 4 in order to guide the endoscope itself to a diseased part in the body cavity. Further, a non-flexible portion 6 is formed at the end of the curved portion 5, in which a video camera, an extractor, a washing nozzle, etc. are disposed. On the other hand, an operation section 7 is provided at the base end of the flexible pipe 4 for adjustment of the bent angle of the curved portion 5 and for other operation. The universal cord 8 is connected to the operation section 7 to transmit video camera signals to the main frame unit 2. Further, although not shown, optical fibers, air and water feeding pipe, wires, etc. are arranged inside the flexible pipe 4.

Figure 2:
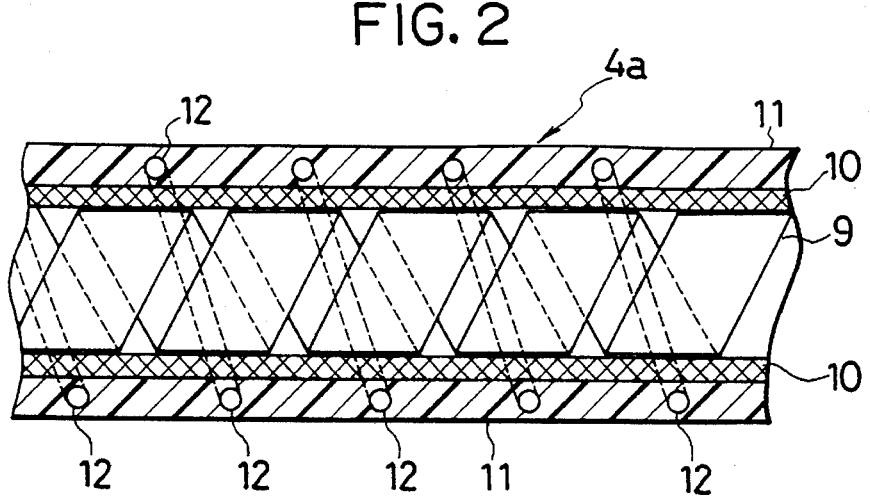
FIG. 2 is a cross-sectional view showing a single segment structure of the flexible pipe used for the first embodiment of the endoscope system according to the present invention.

FIG. 2 shows the structure of a single segment of the flexible pipe 4a adopted for a first embodiment of the endoscope section according to the present invention.

The structure of the flexible pipe 4a is as follows: a metallic helical pipe 9 is covered with a mesh-shaped braid 10, and further the outer circumference of this braid 10 is covered with an outer elastomer cover 11.

A shape memory alloy wire 12 is wound around and buried in the outer cover 11 in spiral fashion being divided into a plurality of segments. If the flexible pipe 4a is 1 m in length and is divided into ten segments S1, S2, ..., S10, for instance, the length of each of the segments is 10 cm.

Figure 3:
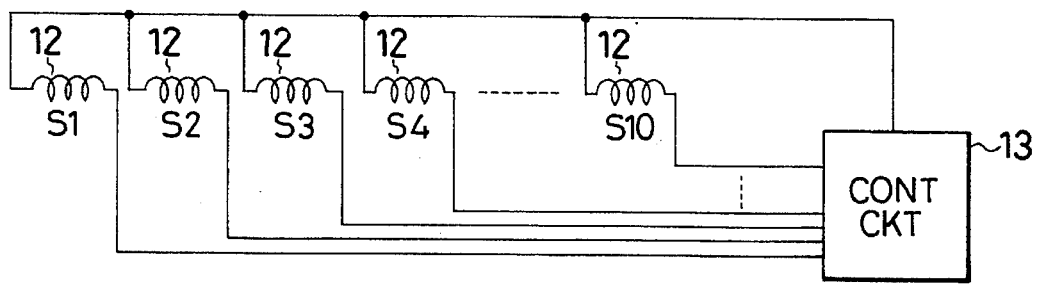
FIG. 3 is a circuit diagram showing a control circuit for controlling current passed through the shape memory alloy wire of the flexible pipe for the first embodiment shown in FIG. 2.

FIG. 3 shows a control circuit 13 for controlling current passed through the shape memory alloy wire 12 provided for each of the segments S1, S2, ..., S10. The shape memory alloy wires 12 of the segments S1, S2, ..., S10 are connected in parallel to constant current sources of the control circuit 13 housed in the main frame unit 2. When some segments required to be hardened are selected by the operation section 7 for instance, current flows through the shape memory alloy wires 12 of the selected segments, so that the shape memory alloy wires 12 of the corresponding segments are hardened.

The shape memory alloy wire 12 is utilized owing to the hardness characteristics dependent upon temperature as follows: When heated by the current flowing therethrough, the shape memory alloy wire 12 is hardened and therefore the shape thereof is stored or held in the high temperature phase (austenite phase) state. At the normal temperature, however, the shape memory alloy wire 12 is softened on the basis of superelasticity in the low temperature phase (martensite phase) state. Further, in this embodiment, the shape memory alloy wire 12 is so designed as to be stored or held in the same spiral shape in both the high and low temperature phase states.

The method of inserting the endoscope into the large intestine will be described hereinbelow.

Figure 5:
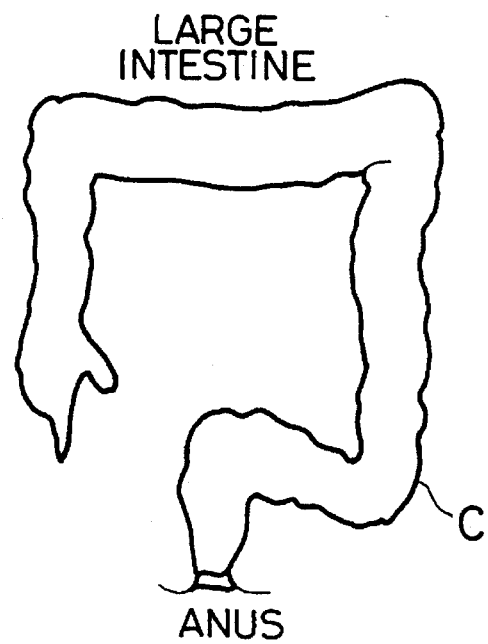
FIG. 5 is an illustration showing the shape of the large intestine.
Figure 6:
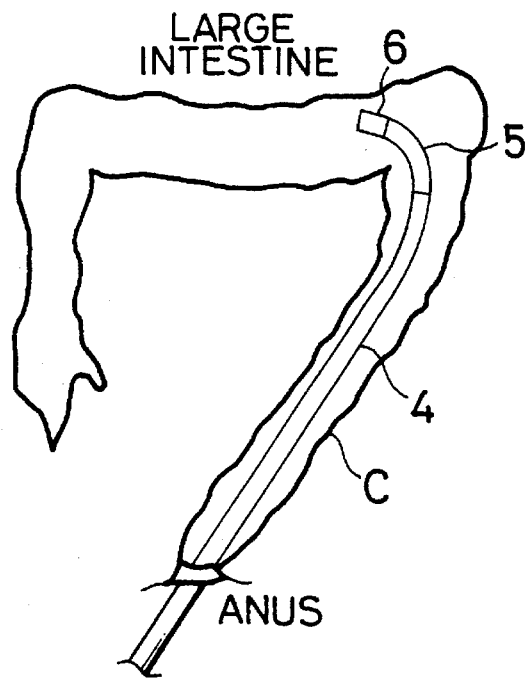
FIG. 6 is an illustration showing the state where the endoscope of the first embodiment has been inserted into the large intestine.

FIG. 5 shows the large intestine, and FIG. 6 shows the state where the endoscope is inserted into the large intestine.

First, without passing current through the shape memory alloy wires 12 of the respective segments, the soft flexible pipe 4 is inserted from the anus to the S-shaped colon C of the large intestine. On the other hand, when the flexible pipe 4 is being passed through the curved portion of the S-shaped colon C, current is passed through the shape memory alloy wires 12 to harden the flexible pipe 4 in a straight line. Under these conditions, since the endoscope 3 is not easily bent and thereby a force can be applied to the end of the endoscope 3, it is possible to easily insert the endoscope 3 through the curved portions of the S-shaped colon C.

Figure 4:
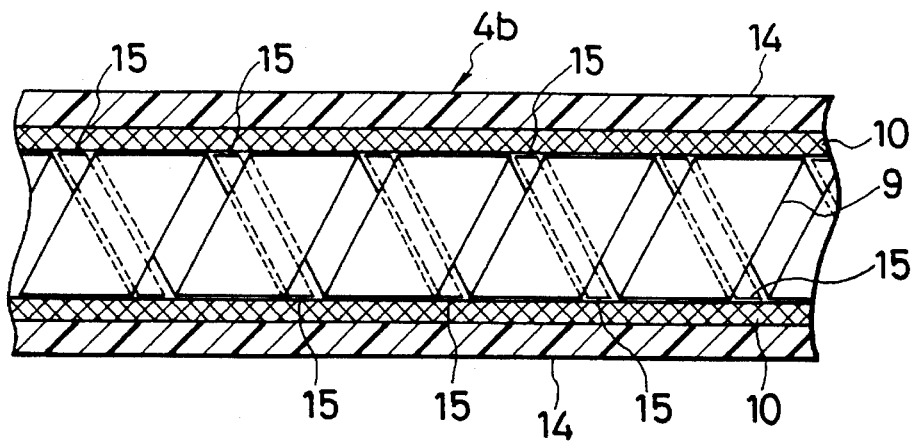
FIG. 4 is a cross-sectional view showing a single segment structure of a modification of the flexible pipe for the first embodiment.

FIG. 4 shows a modification of a single segment of the flexible pipe 4b used for the first embodiment of the endoscope according to the present invention. In the same way as with the case shown in FIG. 2, in the flexible pipe 4b of this modification, a metallic helical pipe 9 is covered with a mesh-shaped braid 10, and further the outer circumference of the braid 10 is covered with an outer elastomer cover 14. Being different from that shown in FIG. 2, however, a spiral shape memory alloy wire 15 is divided into a plurality of segments. and each shape memory alloy wire 15 is provided between gaps of the helical pipe 9 under insulated condition. The current control circuit for controlling current passed through the shape memory alloy wire 15 is the same as that shown in FIG. 3.

SECOND EMBODIMENT

Figure 7:
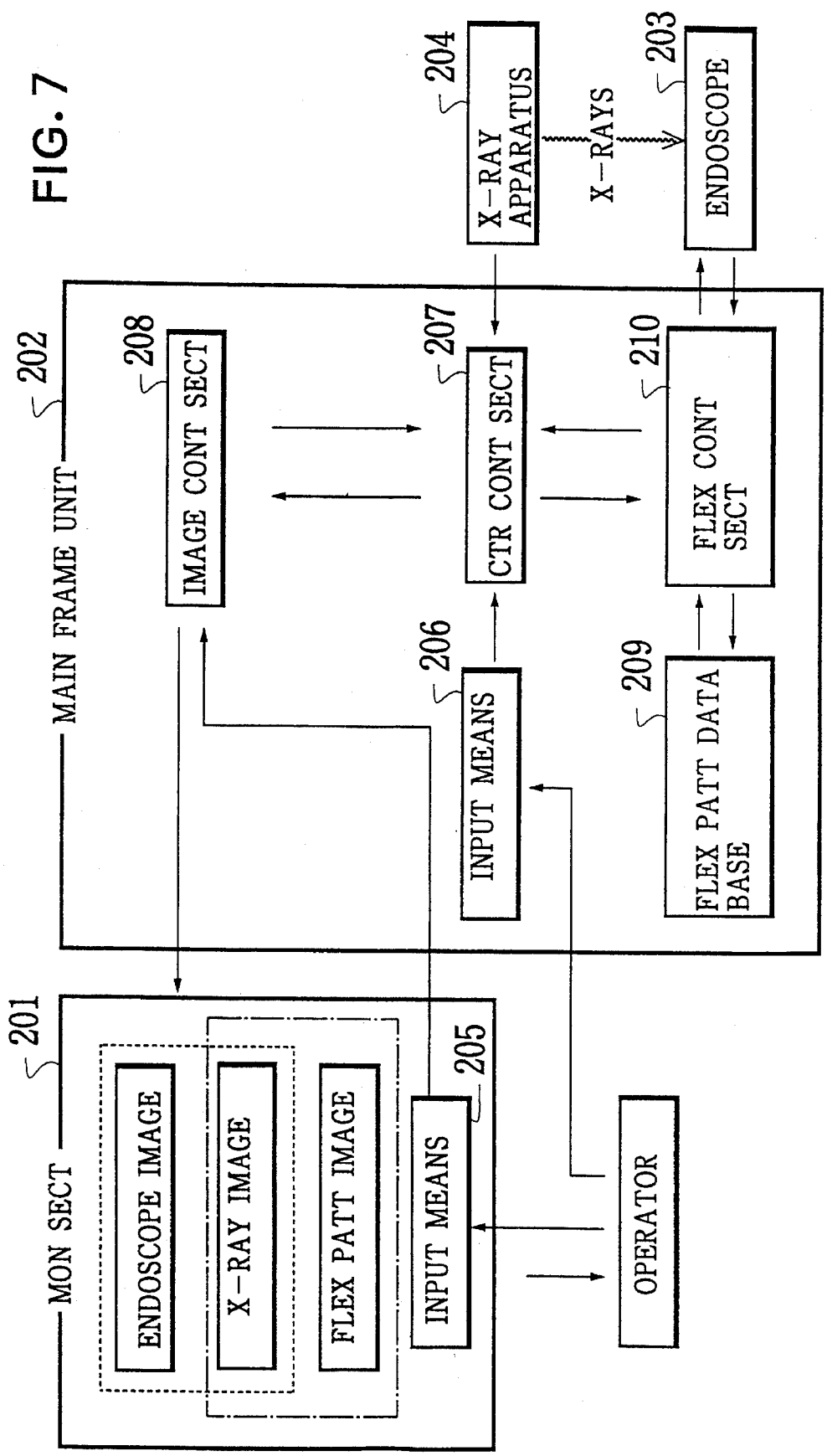
FIG. 7 is a block diagram showing the system configuration of a second embodiment of the endoscope system according to the present invention.

A second embodiment of the endoscope system according to the present invention will be described hereinbelow. With reference to FIG. 7, the endoscope system roughly comprises a monitoring section 201 for displaying internal images of the body cavity acquired through the endoscope and an X-ray fluoroscopic apparatus, and other information; a main frame unit 202 for controlling all the endoscope-related operation including the monitor section 201; and an endoscope section 203 inserted into the body cavity of a patient to be examined to acquire internal images of the body cavity for diagnosis and remedy. Further, the endoscope system is connected to an X-ray fluoroscopic apparatus 204 in order to utilize diagnostic information other than the endoscope. The X-ray fluoroscopic images can be also displayed on the endoscope-monitor section 201 through the main control section 202, as already described. In other words, it is possible to display X-ray fluoroscopic images and flexibility control pattern images (described later) as well as the internal images of the body cavity, independently or simultaneously. In addition, it is possible to directly input Information through the monitor section 201 with the use of inputting means 205 such as a mouse, write pen, touch panel, etc. Here, two or more monitor sections can be used according to the contents to be displayed.

The main frame unit 202 comprises inputting means (keyboard, speech input system, foot switches, etc.) 206 for inputting information required for the endoscope diagnosis and for controlling the flexibility of the endoscope; a central control section 207 for controlling all the system systematically; an image display control section 208 for controlling the image display of the monitor section 201; a flexible pipe flexibility control section 210 for controlling the flexibility of the flexible pipe on the basis of instruction information by the operator and in communication with a flexible pipe flexibility pattern data base 209; and a flexible pipe flexibility pattern data base 209 for storing flexibility control data in the form of patterns to facilitate insertion of the flexible pipe.

In the data base 209, various flexibility patterns are stored so that the flexibility of the flexible pipe can be controlled in accordance therewith according to every possible conditions. In addition to the stored information, the operator can input any desired flexibility control information to the data base 209 so as to be utilized as the new control information for the subsequent diagnosis.

The endoscope section 203 is provided with an image acquiring apparatus for acquiring internal images of the body cavity at the end thereof, so that the interior of the body cavity can be diagnosed and further remedied. A flexible pipe control apparatus (described later) is assembled in the flexible pipe section, so that the flexibility of the flexible pipe can be controlled freely by the endoscope system during diagnosis. Further, the endoscope section 203 is provided with inputting means (not shown). The X-ray fluoroscopic apparatus 204 is connected to the main frame unit 202 of the endoscope system, so that the shape of the flexible pipe within the body cavity of a patient can be checked. In other words, in the endoscope system of the present invention, it is possible to transmit the X-ray fluoroscopic images to the main frame unit 202 of the endoscope system.

In the second embodiment of the endoscope system according to the present invention, since the flexibility of the flexible pipe can be controlled, it is possible to smoothly insert the endoscope into the body cavity of a patient without causing pain to the patient, thus reducing the time required for diagnosis.

In this embodiment, there are two methods of controlling the flexibility of the endoscope flexible pipe as follows: (1) one method is to use the X-ray fluoroscopic image, and (2) the other method is to use the data base of the flexibility of the flexible pipe.

In the first method, it is possible to control the endoscope on the basis of an accurate shape image of the endoscope. In the second method, it is possible to control the endoscope on the basis of the flexibility pattern data, without using the X-ray fluoroscopic apparatus, that is, without exposing the patient to the X-rays. In this second embodiment, although two means for realizing the two methods are incorporated, it is of course possible to realize an endoscope system provided with only any one of the two means according to the demand of the operator.

(1) Method of using X-ray fluoroscopic apparatus

As shown in FIG. 7, the main frame unit 202 of the endoscope system according to the present invention comprises the central control section 207, the flexible pipe flexibility control section 210, the flexible pipe flexibility pattern data base 209, and the image display control section 208.

Figure 8:
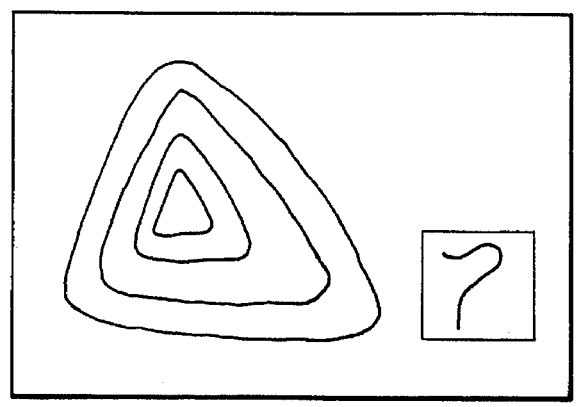
FIG. 8 is an illustration showing images of the endoscope and the shape of the flexible pipe, both displayed on the monitor section shown in FIG. 7.

The information on the shape of the flexible pipe within the interior of the body cavity can be obtained by the X-ray fluoroscopic apparatus 204. The obtained information is transmitted to the monitor section through the central control section 207 and the image display control section 208 to display the shape of the flexible pipe as shown on the right side in FIG. 8. In FIG. 8, the endoscope image is shown as a large picture and the X-ray fluoroscopic image is shown as a small picture. However, these images can be switched from the large picture to the small picture or vice versa.

Figure 9:
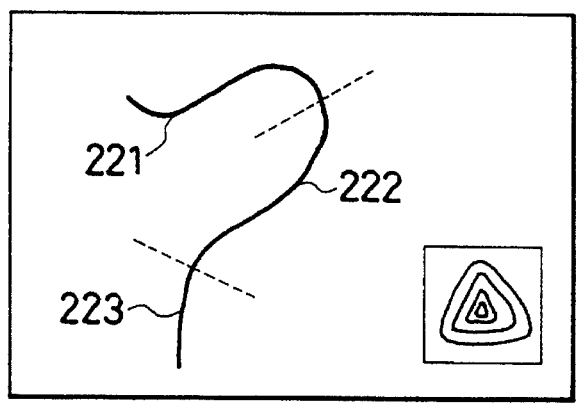
FIG. 9 is a similar illustration showing images of the endoscope and the shape of the flexible pipe, both displayed on the monitor section shown in FIG. 7.

Here, the operator switches the X-ray fluoroscopic image to the large picture and the endoscope image to the small picture. In this display, the X-ray fluoroscopic image is displayed by indicating boundary lines between two adjoining segments as shown in FIG. 9, in which numerals 221, 222 and 223 denote the segments. With reference to the image as shown in FIG. 9, the operator inputs a numerical value of the segment whose flexibility is required to change and the flexibility thereof through the inputting means (e.g., mouse, write pen, etc.) 205 of the monitor section 201 or the inputting means (e.g., button of the endoscope, keyboard, speech, etc.) 206 of the main frame unit 202. The input information is transmitted to the flexible pipe flexibility control section 210 through the central control section 207. The flexible pipe flexibility control section 210 outputs a flexibility control signal to the endoscope section 203 to change the flexibility of the flexible pipe in accordance with a predetermined pattern. Thereafter, the operator observes the easiness of endoscope insertion on the basis of the endoscope image or the X-ray fluoroscopic image. If the easiness thereof is not sufficient, the operator decides the optimum flexibility pattern by repeating the above-mentioned procedure. That is, if the easiness of the endoscope insertion cannot be improved, the numerical values of the segment whose flexibility is required to change and of the flexibility thereof are selected repeatedly, until the easiness of the endoscope insertion can be improved.

Figure 10:
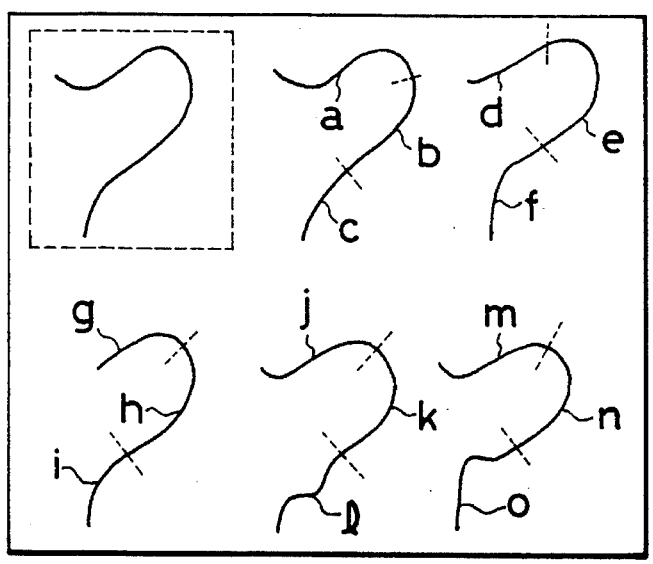
FIG. 10 is an illustration showing the flexibility patterns displayed on the monitor section shown in FIG. 7.

In this procedure, it is also possible to improve the easiness of the endoscope insertion by reading the past flexibility pattern, used under the similar positional condition of the endoscope now displayed as the X-ray fluoroscopic image on the monitor section 201, from the flexible pipe flexibility pattern data base 209. The flexibility patterns are displayed as shown in FIG. 10, in which the symbols a to o denote numerical values representative of the flexibility quantitatively. The operator decides a flexibility pattern to be adopted on the basis of the X-ray fluoroscopic image and the flexibility patterns of the flexible pipe flexibility pattern data base 209. The flexibility pattern can be inputted through the inputting means (e.g., mouse, write pen, etc.) 205 of the monitor section or the inputting means (e.g., button of the endoscope, keyboard, speech, etc.) 206 of the main frame unit 202. The inputted information is transmitted to the flexible pipe flexibility control section 210 through the central control section 207. The flexible pipe flexibility control section 210 outputs a flexibility control signal to the endoscope section 203 to change the flexibility of the flexible pipe in accordance with a predetermined pattern. After the flexibility pattern has been changed, the operator observes the easiness of endoscope insertion on the basis of the endoscope image or the X-ray fluoroscopic image. If the easiness thereof is still not sufficient, the operator decides the optimum flexibility pattern by repeating the above-mentioned procedure. In this case, if the easiness of the endoscope insertion cannot be improved even after all the patterns of the flexible pipe flexibility pattern data base 209 have been tried, it is also possible to form an operator's own flexibility pattern to improve the easiness of the endoscope insertion, by inputting the numerical values of the flexibility of the respective segments of the flexible pipe through the respective inputting means 205 and 206. The newly formed flexibility pattern can be inputted to the flexible pipe flexibility pattern data base 209 so as to be utilized in the succeeding examination.

In addition to the above-mentioned means, it is also possible to realize an endoscope system incorporated with another diagnostic apparatus such as CT, MRI, or ultrasonic apparatus. Further, it is also possible to construct the endoscope system in such a way that a three-dimensional image of the large intestine is previously stored in the data base as patient information or otherwise the data acquired by the CT, MRI or ultrasonic diagnostic apparatus are directly exchanged between the endoscope system and the other diagnostic apparatus, In such a way that the data acquired by the other apparatus can be utilized effectively during the endoscope insertion.

(2) Method of using flexible pipe flexibility data base

In this method, the operator can improve the easiness of the endoscope insertion by freely controlling the endoscope in accordance with the data base including the endoscope control information optimum to the diagnosis situation, without use of the X-ray fluoroscopic image.

Figure 11:
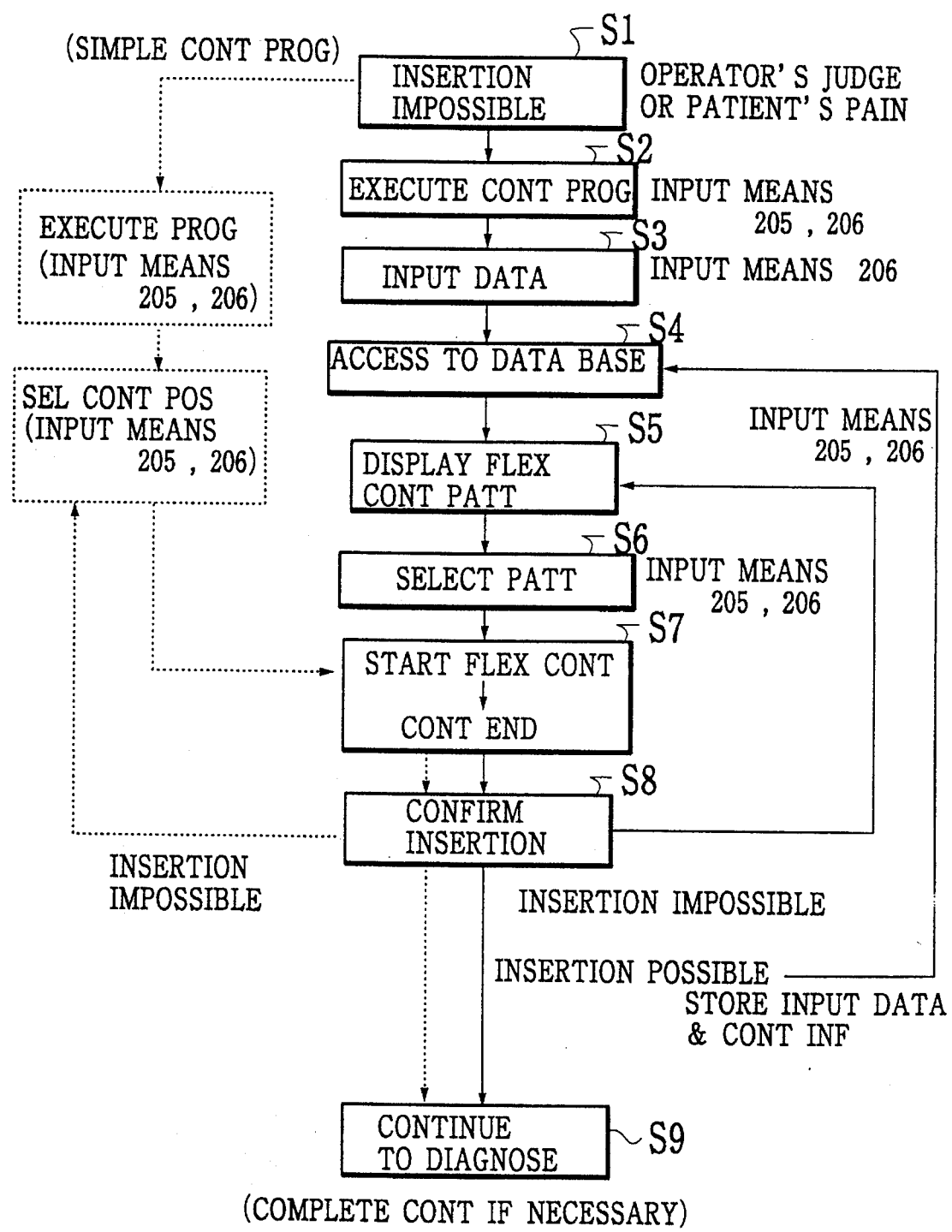
FIG. 11 is a flowchart for assistance in explaining the procedure of using the second embodiment of the endoscope system according to the present invention.
Figure 12:
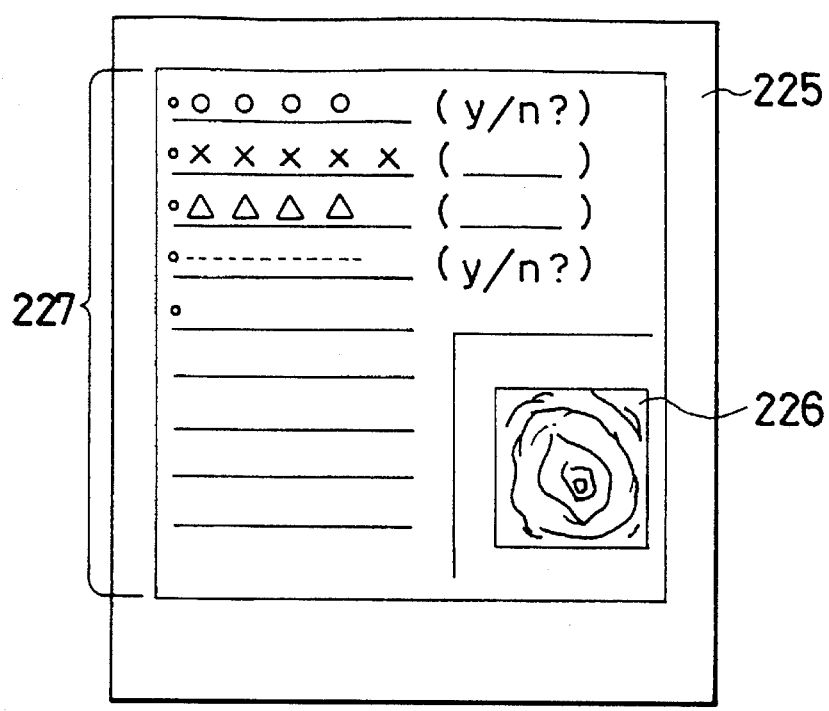
FIG. 12 is an illustration showing an image of the endoscope displayed as a small picture and an image of the menu for inputting control information displayed as a large picture on the monitor section shown in FIG. 7.
Figure 13:
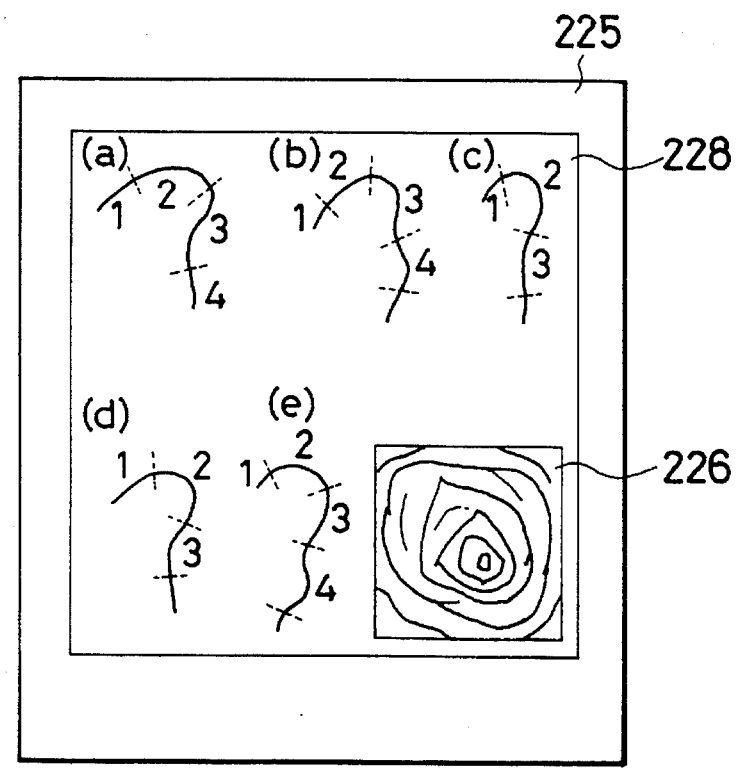
FIG. 13 is an illustration showing an image of the endoscope displayed as a small picture and an image of the flexibility patterns displayed as a large picture on the monitor section shown in FIG. 7.
Figure 14:
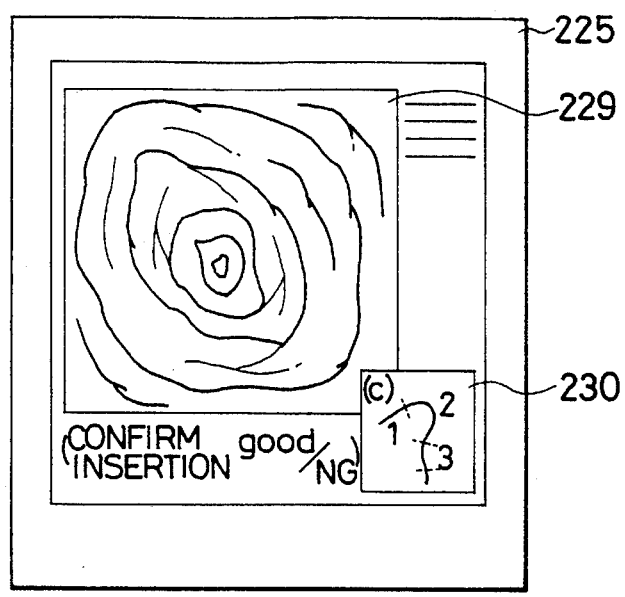
FIG. 14 is an illustration showing an image of the shape of the flexible pipe as a small picture and an image of the endoscope displayed as a large picture on the monitor section shown in FIG. 7.

FIG. 11 is a flowchart for assistance in explaining the procedure of the present embodiment. The assumption is made that during the diagnosis, a part of the flexible pipe of the endoscope is bent and therefore it is difficult to further insert the endoscope, so that the patient complains a pain (in step S1). In this case, the operator inputs an instruction of executing a flexible pipe control program through the endoscope 203, the inputting means 205 of the monitor section 201, or the inputting means 206 of the main frame unit 202 (in step S2). In this case, the monitor picture 225 is changed as shown in FIG. 12, in which the endoscope image is displayed as a small picture 226 and a menu of inputting control information is displayed as a large picture 227. In accordance with the displayed menu, the operator inputs the diagnosis situation and the endoscope situation as data through the inputting means 206 of the main frame unit 202 (in step S3). Here, the data are a length of the inserted endoscope; an end position of the endoscope determined by the image; an easiness of movement of the end portion of the endoscope such as pulling-in or -out, twisting, etc.; a position at which the patient feels a pain or a pressure; and other information data. After all the data have been inputted, all the data are transmitted to the data base 209 through the flexible pipe flexibility control section 210 (in step S4). The data base 209 compares the inputted data with all the control patterns already stored, and displays some of the flexible pipe flexibility control patterns 228 suitable for the current situation on the monitor section 201 as shown in FIG. 13 (in step S5). In this step, each of the control pattern images includes a control rate and a control distribution of the flexible pipe flexibility determined for each segment. Here, the operator selects a pattern most suitable for the current situation on the basis of the diagnosis situation and the patient's information (in step S6). In accordance with the ,selected pattern, the endoscope is controlled by the flexible pipe flexibility control section 210 (in step S7). At the same time, the monitor picture is changed as shown in FIG. 14, in which the endoscope image is displayed as the large picture and the flexible pipe control situation information is displayed as the small picture, thus indicating the completion of the flexible pipe flexibility control. Upon the confirmation of the control end, the operator inserts the endoscope. In this case, if the endoscope can be inserted, the operator transmits an end of the flexible pipe control program to the central control section 207 through the inputting means 205 or 206 of the monitor section 201, the main frame unit 202 or the endoscope 203. Then, the control data and the input data are stored in the data base 209 as new flexible pipe flexibility control information. Further, if the endoscope cannot be inserted, the operator transmits an information data indicative of that the endoscope insertion is impossible to the flexible pipe flexibility control section 210 through the inputting means 205 or 206 of the main frame unit 202, the monitor section 201 or the endoscope 203, so that the picture is returned again to that as shown in FIG. 13. In this case, the flexibility control pattern on which the endoscope cannot be inserted is deleted from the picture. Further, after the endoscope can be inserted, the diagnosis is continued (in step S9). In this case, however, it is preferable to end the flexible pipe control program as occasion demands.

Further, in the endoscope system of the present invention, it is possible to previously store the simplified flexible pipe flexibility control pattern obtained by dividing the flexible pipe into several segments on the basis of the operator decision. Therefore, when the endoscope cannot be inserted, it is possible to roughly control the flexible pipe of the endoscope without inputting data.

Figure 15:
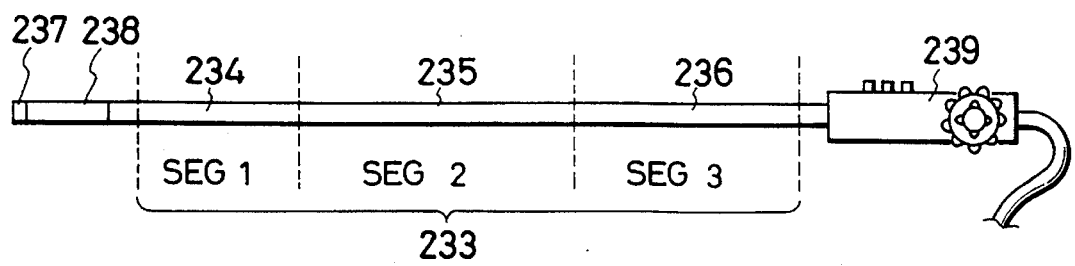
FIG. 15 is a side view showing an example of the endoscope section of the second embodiment.
Figure 16:
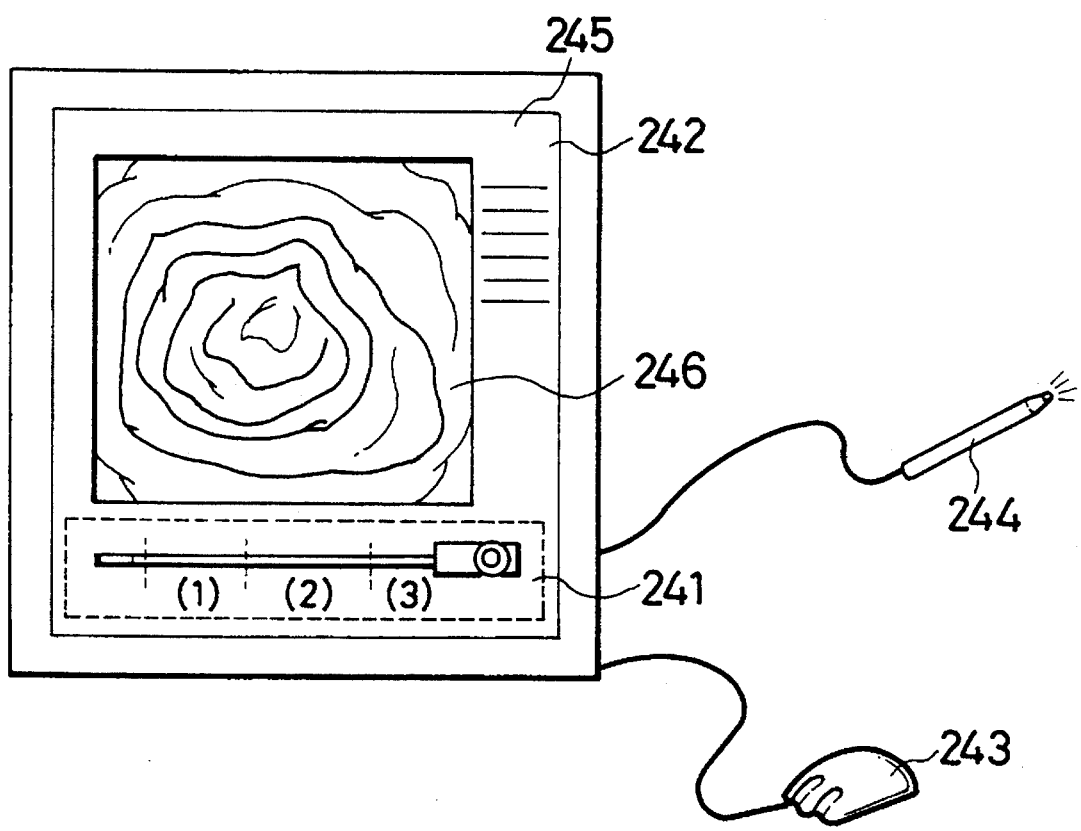
FIG. 16 is a front view showing an exemplary image of the monitor section of the second embodiment.

FIG. 15 shows an example of the endoscope, which is roughly composed of a flexible pipe 233, an end portion 237, a curved portion 238, and an operation portion 239. Further, the flexible pipe 233 is divided into three segments of an end side 234, an intermediate portion 235 and an operation side 236 in such a way that the flexible pipe flexibility can be controlled. In use of the endoscope system, when the operator decides that the endoscope insertion is impossible, the simplified control program stored in the main frame unit 202 is executed through the inputting means 205 or 206. Then, the central control section 207 switches the picture to that as shown in FIG. 16 through the image display control section 208. On the basis of a model image 241 of the endoscope displayed on the monitor section 201, the operator selects any segments whose flexibility is required to be controlled and transmits the control instructions related thereto by the use of a mouse 243, a write pen 244 directly on the monitor picture 242 or with the use of a panel switch method 245 on the picture. In FIG. 16, the numeral 246 denotes an endoscope image. Further, the control information inputting means are a foot switch, a keyboard of the main frame unit, or a speech, etc. When inputted the control information representative of the selected segments is transmitted to the flexible pipe flexibility control section 210, and further directly to the endoscope for controlling the endoscope. Further, the end of the control is discriminated when the picture formation is returned to the ordinary endoscope image display mode.

Figure 17:
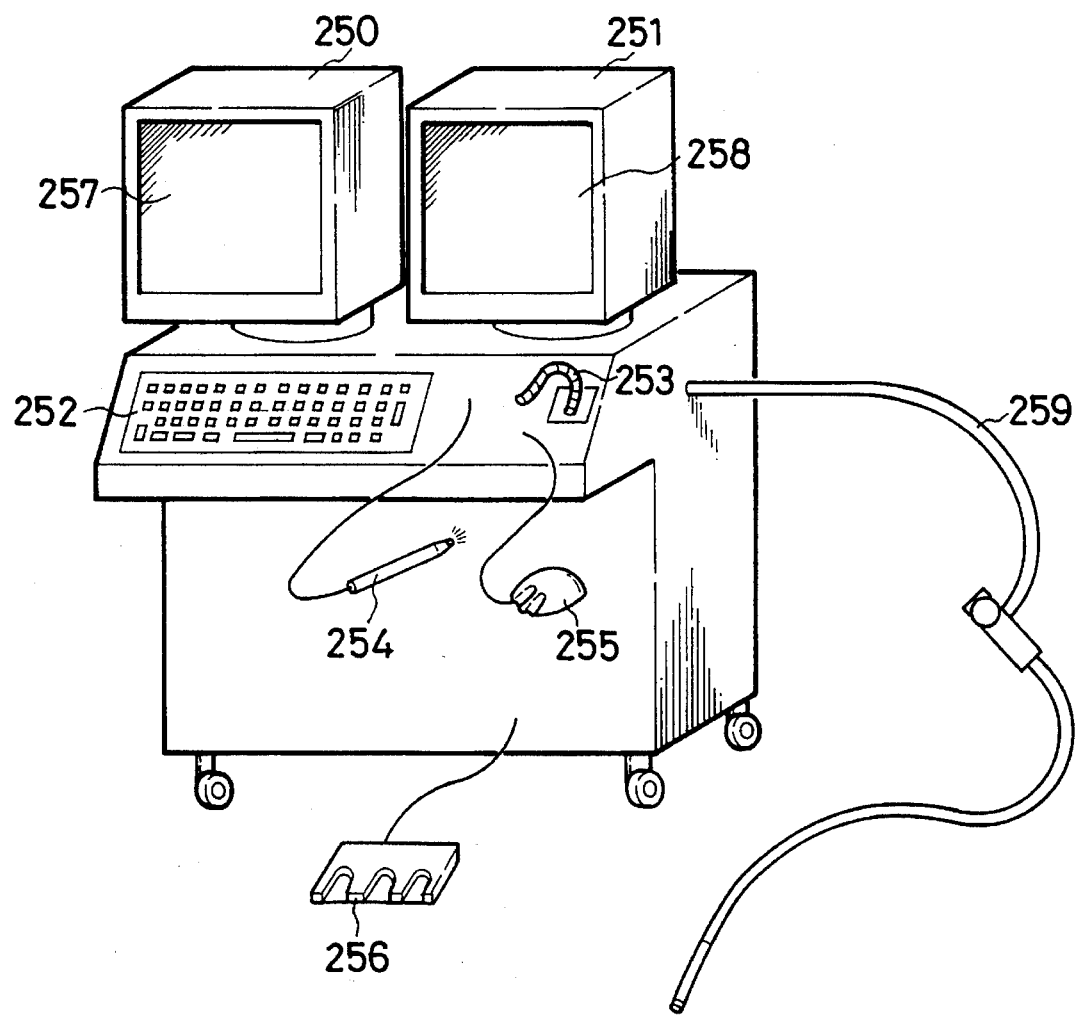
FIG. 17 is a general view showing the second embodiment of the endoscope system of two monitor type according to the present invention.

In the above-mentioned embodiment, only a single monitor is used and the picture formation is switched to input the control information through the monitor. However, a plurality of monitors can be used together to display the endoscope image, to input the control information, to display and select the control patterns, etc., separately. FIG. 17 shows an example of two monitor endoscope system, in which an endoscope image monitor 250 and a flexibility control information monitor 251 are provided independently. Further, a keyboard 252, a speech inputting microphone 253, a write pen 254, a mouse 255, a foot switch 256, a touch sensor type panels 257 and 258 are provided as the inputting means. In addition, it is also possible to mount a simple inputting device on the endoscope 259 itself.

According to the above-mentioned embodiment such that the flexibility can be controlled by inputting control information, it is possible to control the flexibility accurately according to the situation. Further, when the simplified control method is adopted, it is possible to reduce the diagnosis time and therefore improve the diagnosis efficiency.

In the endoscope system according to the present invention, since the endoscope can be always inserted during diagnosis, it is possible to perform the diagnosis and remedy smoothly without causing pain to the patient, and further to reduce the diagnosis time.

THIRD EMBODIMENT

Figure 18:
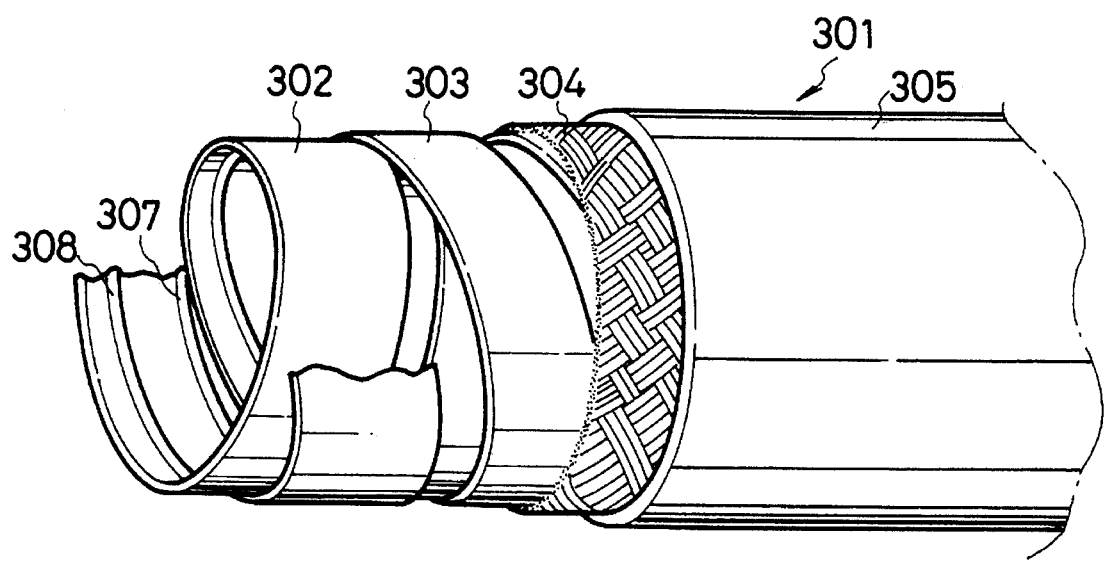
FIG. 18 is an enlarged broken view showing the structure of a third embodiment of the flexible pipe of the endoscope system according to the present invention.

In this embodiment, the shape memory alloy is used to control the flexibility of the flexible pipe. FIG. 18 shows the structure of the flexible pipe of the endoscope of this embodiment. The flexible pipe 301 is composed of an innermost helical pipe 302 of the shape memory alloy, a metallic helical pipe 303 disposed on the outer surface of the helical pipe 302, an outer metallic mesh-shaped braid 304 disposed on the outer circumferential surface of the helical pipe 303, and an outermost elastomer 305 disposed so as to cover the braid 304. Here, the helical direction of the innermost pipe 302 of the shape memory alloy is opposite to that of the metallic helical pipe 303. Further, two small-diameter hollow tubes 307 and 308 formed of a metal (e.g., copper) of high thermal conductivity are attached in tight contact with the inside surface of the helical pipe 302 of the shape memory alloy. The helical pipe 302 formed of the shape memory alloy is covered throughout by an insulating heat-resistant resin or an insulating ceramic so as to be insulated electrically from the metallic helical pipe 303 and the contents disposed or passed therethrough.

Figure 19:
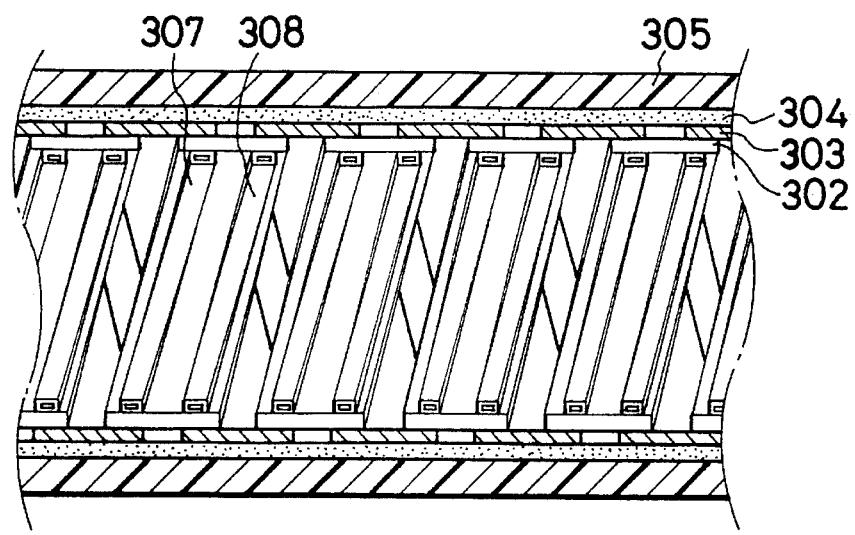
FIG. 19 is a longitudinal cross-sectional view showing the flexible pipe shown in FIG. 18.

FIG. 19 shows the cross section of the flexible pipe 301. The outer elastomer cover 305 and the mesh-shaped braid 304 are brought into tight contact with respect to each other so as not to slide at the boundary portion thereof. The outer diameter of the metallic helical pipe 303 is determined to be equal to the inner diameter of the braid 304. Therefore, the helical pipe 303 and the braid 304 are only in contact with each other at the contact surface between both so as to be slidable freely relative to each other when the flexible pipe 301 is bent.

The outer diameter of the helical pipe 302 of the shape memory alloy is determined to be equal to the inner diameter of the metallic helical pipe 303 at the normal low temperature (in the martensite phase). Therefore, the helical pipe 302 and the metallic helical pipe 303 are only in contact with each other at the contact surface between both so as to be slidable freely relative to each other. On the other hand, this helical pipe 302 of the shape memory alloy stores an outer diameter slightly larger than the inner diameter of the metallic helical pipe 303 at the high temperature (in the austenite phase).

When cooled from the high temperature at which the shape is stored (the austenite phase), the shape memory alloy changes to the martensite phase at and below the martensite transformation end temperature (Mf). On the other hand, when heated from the low temperature (in the martensite phase), the shape memory alloy changes to the austenite phase at and above the inverse transformation temperature (Af) and returns to the shape memory state. In the case of Ni—Ti alloy, the above-mentioned transformation temperature changes according to the concentration of Ni. When the Ni concentration is set between 48 and 50 at. %, it is possible to determined the transformation temperature within a range between 50° and 60° C.

The shape memory alloy is heated by Joule heat generated when current is passed through the alloy. On the other hand, the shape memory alloy is cooled by the water flowing through the two cooling tubes 307 and 308 attached to and along the inner surface of the helical shape memory alloy 302.

Figure 20:
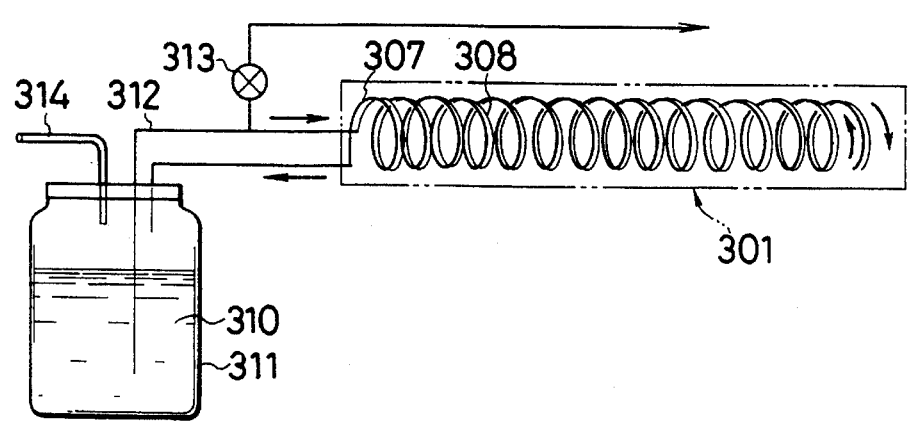
FIG. 20 is an illustration showing a pipe line system of cooling water passed through the flexible pipe shown in FIG. 18.

FIG. 20 shows the method of flowing cooling water through the tubes 307 and 308. Two inner ends of the two cooling tubes 307 and 308 are attached to the inner surface of the helical pipe 302 of the shape memory alloy, and connected at the inner end portion of the flexible pipe 301. Further, water is fed through the tube 308 and returned through the tube 307. The water 310 used for cooling the helical alloy pipe 302 is water for washing a lens of the endoscope, for instance. The cooling water is fed from a water bottle 311 disposed in the endoscope body, through a water feed tube 312 and a universal cord, into the endoscope. Within the endoscope, the universal cord is branched to a washing tube for washing the lens of the endoscope and the cooling tubes 307 and 308 of the flexible pipe 301. The cooling water is circulated into the water bottle 311 through the two cooling tubes 307 and 308. Further, the water feeding tube 312 is connected to a water nozzle through a water valve 313. Further, in FIG. 20, the reference numeral 314 denotes an air supply passage.

When current is passed through the helical pipe 302 of the shape memory alloy, since the temperature of the pipe 302 rises, the diameter of the helical pipe 302 increases at a temperature beyond the transformation temperature Af, so that the metallic helical pipe 303 is brought into pressure contact with the braid 304. In this state, since the frictional force in the contact surface between the helical pipe 302 of the shape memory alloy and the metallic helical pipe 303 and the frictional force in the contact surface between the metallic helical pipe 303 and the braid 304 both increase, these pipes are not slid relative to each other. In addition, the helical pipe 302 itself is hardened due to the characteristics of the shape memory alloy. That is, since the friction in the contact surfaces between the helical pipe 303 and the braid 304 increases, and in addition since the innermost helical pipe 302 is hardened, the flexible pipe 301 becomes difficult to be bent. On the other hand, when current is not passed through the shape memory alloy, since the temperature thereof drops by the cooling water, the shape memory alloy transforms from the austenite phase to the martensite phase at and below Mf, so that the outer diameter of the shape memory alloy helical pipe 302 is reduced so as to be equal to the inner diameter of the metallic helical pipe 303. Accordingly, the friction in the contact surface between the helical pipe 303 and the braid 304 decreases, with the result that the helical pipe 303 and the braid 304 can be slid relative to each other. At the same time, since the shape memory alloy transforms to the martensite phase, the shape memory alloy is softened. As described above, the flexible pipe 301 becomes soft and therefore bendable.

Figure 21:
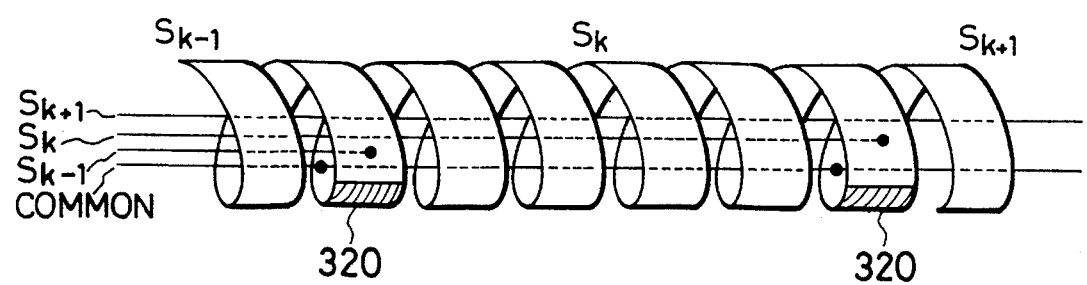
FIG. 21 is an illustration for assistance in explaining the method of dividing the helical pipe of the flexible pipe shown in FIG. 18 into segments.
Figure 22:
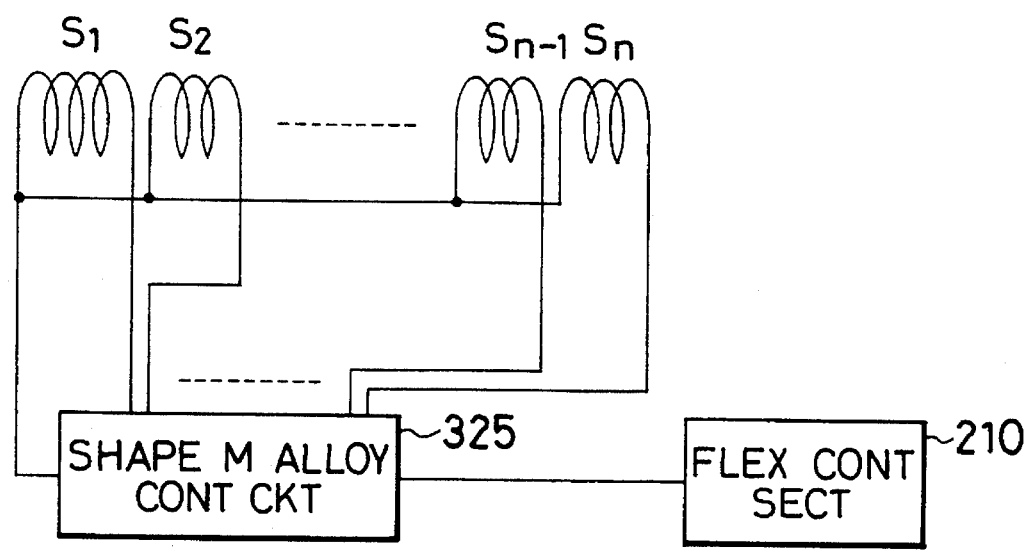
FIG. 22 is a block diagram showing the control circuit for controlling the respective segments of the helical pipe shown in FIG. 21.

In order to harden some parts of the flexible pipe 301 selectively, the flexible pipe 301 is divided into several segments. FIG. 21 shows the method of dividing the flexible pipe into segments $S_{k-1}$, $S_k$, $S_{k+1}$. An insulator 320 is provided between the two adjacent segments to insulate the two segments electrically and further to pass current each of the segments independently. FIG. 22 is a block diagram showing a control circuit 325 for passing current through each of the segments. In response to a command applied from the flexible pipe flexibility control section 210 of the main frame unit 202, a shape memory alloy control circuit 325 passes current through only the shape memory alloy of the segments required to be hardened. In this case, it is of course possible to select a plurality of segments to be heated simultaneously.

FOURTH EMBODIMENT

In this fourth embodiment, a specific elastomer is used, whose elastic modulus can be adjusted without changing the volume of the outer elastomer cover of the flexible pipe. In more detail, the flexible pipe is divided into several segments. An electrode is attached to an inner side surface and an outer side surface of the outer elastomer cover of each segment, and a voltage is applied between both the electrodes to change the elastic modulus of the elastomer of the outer cover. During the examination, when the endoscope is being passed through a part at which the flexible pipe is easily bent, a voltage is applied to the segments to increase the elastic modulus of the elastomer of the outer cover now passing through this part, so that the flexible pipe is not bent easily. After having passed through the part at which the flexible pipe may be bent, the voltage is released to return the flexible pipe to the ordinary flexible state.

Figure 23:
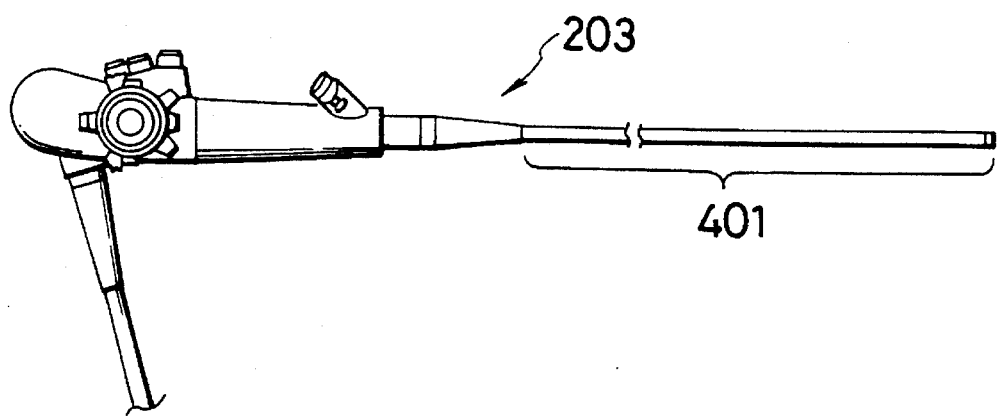
FIG. 23 is a side view showing a fourth embodiment of the endoscope section of the endoscope system according to the present invention.

FIG. 23 shows an endoscope section 203 of the endoscope system of this embodiment, in which a flexible pipe 401 of the above-mentioned method is adopted.

Figure 24:
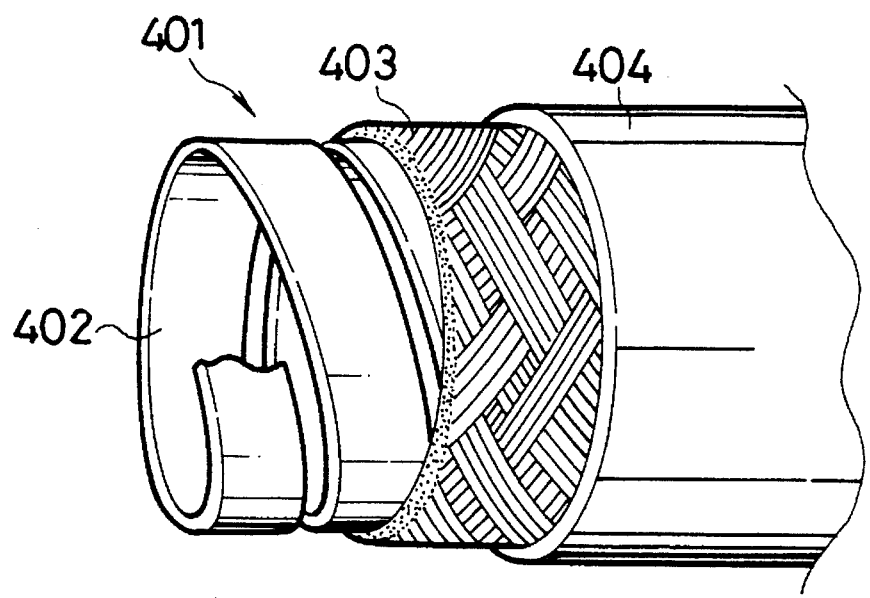
FIG. 24 is an enlarged broken view showing the structure of the fourth embodiment of the flexible pipe of the endoscope system.

FIG. 24 shows the structure of this flexible pipe 401, in which the flexible pipe 401 is composed of a metallic helical pipe 402, a metallic mesh-shaped fiber 403, and an outer cover of elastic member (the outer cover is formed of the elastomer in this embodiment) 404.

Figure 25:
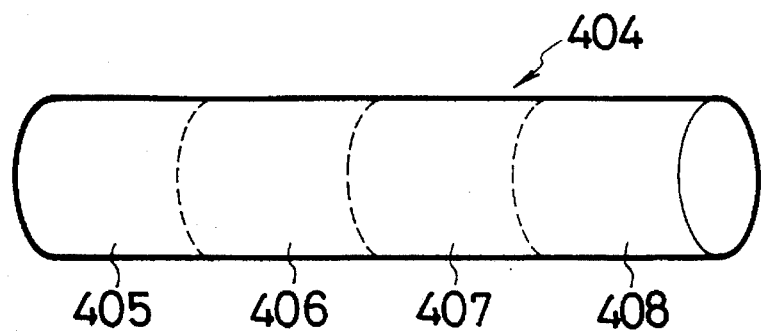
FIG. 25 is an illustration showing the state where the outer elastomer cover of the flexible pipe shown in FIG. 24 is divided into segments.

FIG. 25 shows the state where the outer elastomer cover 404 of elastic member is divided into four segments 405, 406, 407 and 408. In this drawing, although the number of the segments is four, the outer elastomer cover 404 can be of course divided into four or more segments.

Figure 26:
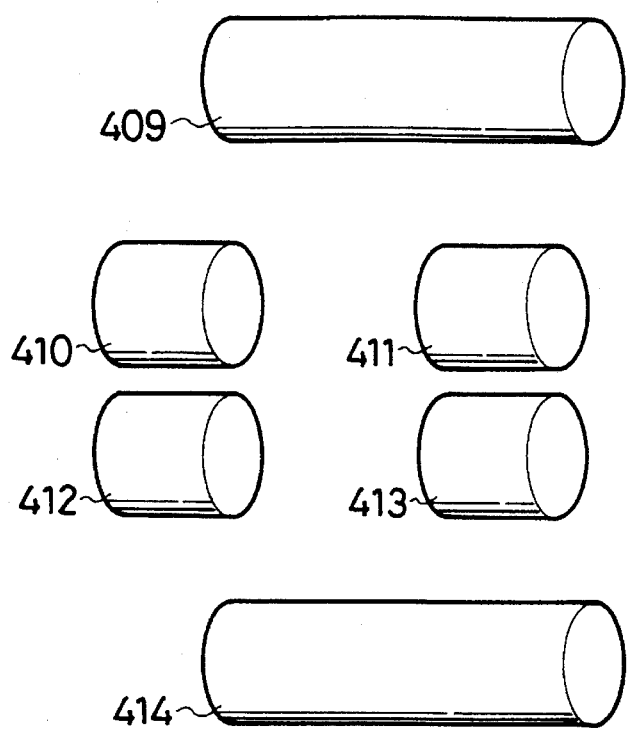
FIG. 26 is an illustration for assistance in explaining the segment structure of the outer elastomer cover shown in FIG. 25.

FIG. 26 shows the structure of the outer elastomer cover 404 of the respective segments shown in FIG. 25. Each segment is composed of three elastomer layers of an outermost elastomer layer 409, an intermediate elastomer layer 410, 411, 412 or 413, and an innermost elastomer layer 414. Here, only the intermediate elastomer layer is made of a specific elastomer whose elastic modulus can be changed.

Figure 27:
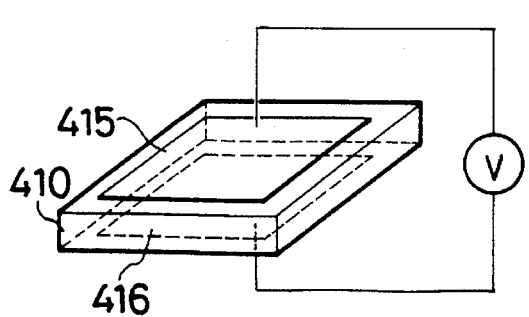
FIG. 27 is an illustration for assistance in explaining the method of modifying the elastic modulus of the elastomer of the intermediate layer shown in FIG. 26.

FIG. 27 shows the method of changing the elastic modulus of the intermediate specific elastomer layer 410 to 413. The specific elastomer 410 (representative of other intermediate layers 411 to 413) whose elastic modulus can be changed is a substance such that polycobaltmethacrylate is fixed with isoprene rubber, for instance. Two electrodes (e.g., foil) 415 and 416 are attached to both upper and lower surfaces of this elastomer layer 410. When a voltage is applied between the two electrodes 415 and 416, the elastic modulus of the elastomer changes according to the magnitude of the voltage. Under these conditions, the volume of the elastomer will not change and further no current flows therethrough.

Figure 28:
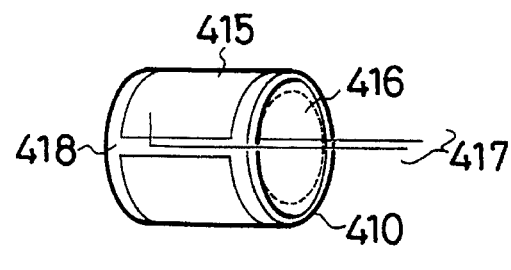
FIG. 28 is an illustration showing the state where two opposing electrodes are mounted on the elastomer of the intermediate layer shown in FIG. 26.

FIG. 28 shows the actual electrodes formed on the intermediate elastomer layer. On the other hand, FIG. 27 is a development view showing the electrodes shown in FIG. 28 in a sheet state. As already described, foil-shaped electrodes 415 and 416 are attached to the inner and outer circumferential surfaces of the cylindrical elastomer 410. Further, an area 418 for laying each electrode wire 417 is provided on both the circumferential surface of the cylindrical elastomer 410.

Figure 29:
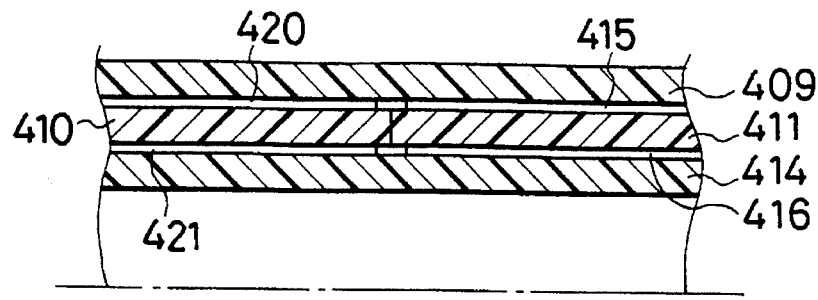
FIG. 29 is an enlarged partial cross-sectional view showing the three-layer structure of the outer elastomer cover shown in FIG. 25.

FIG. 29 is a cross-sectional view showing the three-layer elastomer structure, in which an junction portion between the two intermediate specific elastomer layers 410 and 411 is shown by way of example. In FIG. 29, two electrodes 415 and 416 are attached to the inner and outer circumferential surfaces of the intermediate specific elastomer layer 411, and other two electrodes 420 and 421 are attached to the inner and outer circumferential surfaces of the intermediate specific elastomer layer 410. Here, a space is provided between the two adjacent outer electrodes 415 and 420 and between the two adjacent inner electrodes 416 and 421, respectively. Further, heat-shrinkable tube-shaped elastomer is used for the intermediate specific elastomer layers 410 and 411, and an insulating elastomer is used for the innermost and outermost elastomer layers 409 and 414, respectively.

Figure 30:
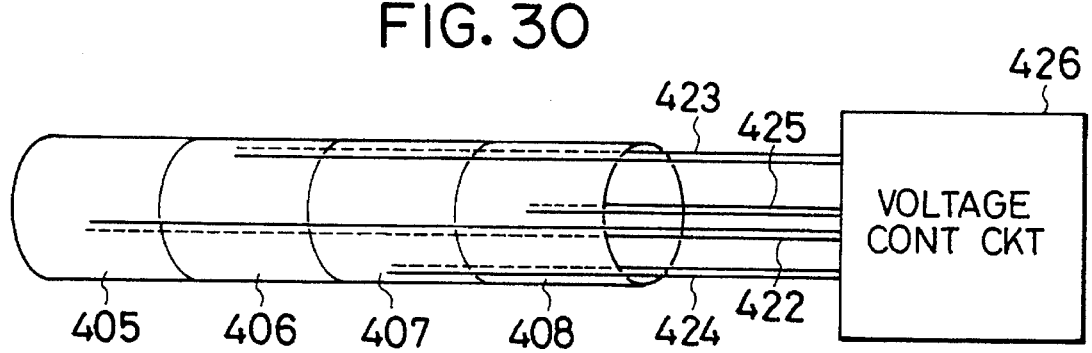
FIG. 30 is a diagram showing the system for supplying voltages to the respective segments of the outer elastomer cover shown in FIG. 25.
Figure 31:
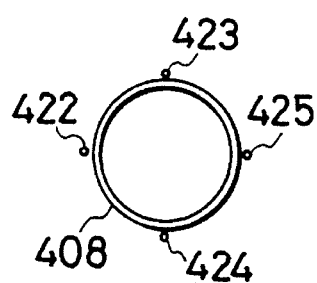
FIG. 31 is a view for assistance in explaining the arrangement of electrode wires disposed on the outer circumference of the outer elastomer cover shown in FIG. 30.

FIG. 30 shows the wiring structure of pairs 422, 423, 424 and 425 of the electrode wires provided for the segments 405, 406, 407 and 408, respectively, in which only the intermediate layers are shown for brevity. These electrode wires are arranges so as not to be In contact with each other. For instance, if the flexible pipe 4 is divided into four segments, pairs of the electrode wires are arranged at regular angular intervals of 90 degrees along the outer circumferential surface of the intermediate specific elastomer layer, as depicted in FIG. 31. Further, it is possible to use the ground side electrode wires in common to make the best use of the space of the narrow flexible pipe. In this case, it is preferable to arrange the ground side wires of the electrode (the electrode 415 in FIG. 28) on the outer surface of the intermediate elastomer layer for safety. As shown in FIG. 30, these electrode wires are connected to a voltage control circuit 426 for controlling the voltages applied to the electrode wires, respectively.

As shown in FIG. 7, the endoscope system comprises the endoscope section 203 and the main frame unit 202. Further, the main frame unit 202 comprises the central control section 207, the flexible pipe flexibility control section 210, the flexible pipe flexibility pattern data base 209, and the image display control section 208. Here, the voltage control circuit 426 shown in FIG. 30 is a part of the flexible pipe flexibility control section 210. The operator recognizes the shape of the flexible pipe 401 in the interior of the body cavity on the basis of the X-ray fluoroscopic image or estimates the same on the basis of the image of the flexible pipe flexibility pattern data base 209, and decides the flexibility pattern to be now adopted. The information related to the decided flexibility pattern is transmitted to the flexible pipe flexibility control section 210 via the central control section 207 to change the flexibility of the flexible pipe 401.

Figure 32:
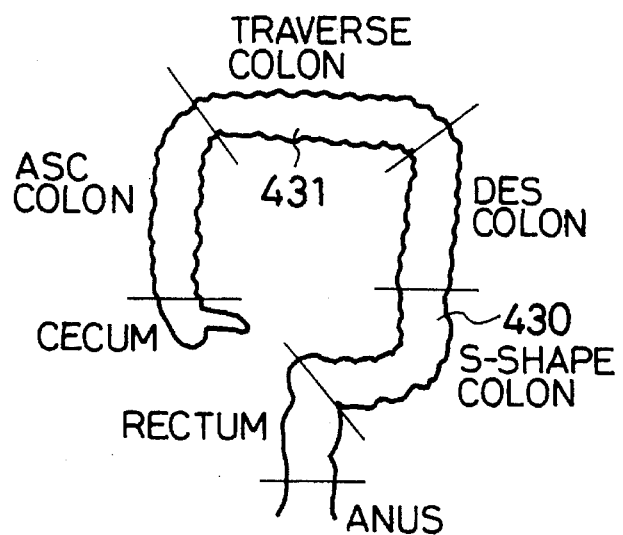
FIG. 32 is an illustration showing the large intestine.

The function of the endoscope system of the present embodiment used for large intestine examination will be described herein below with reference to FIGS. 32, 33, 34 and 35. FIG. 32 shows the structure of the large intestine, in which both the S-shaped colon 430 and the traverse colon 431 are not fixed to the abdominal wall and therefore movable.

Figure 33:
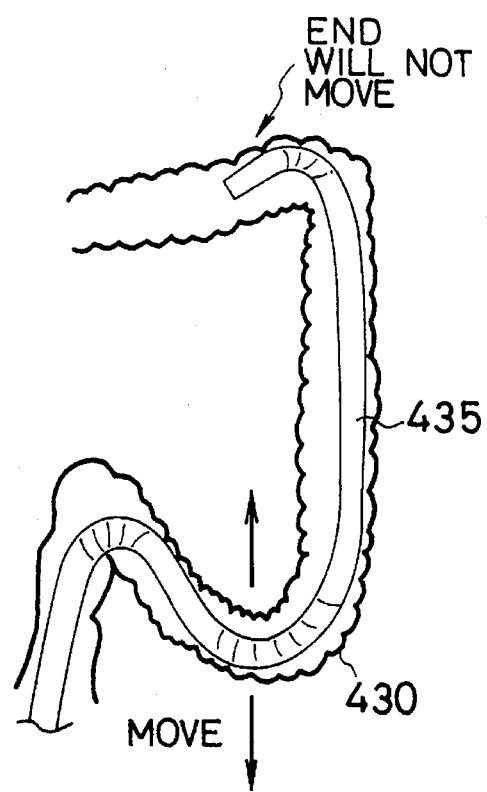
FIG. 33 is an illustration for assistance in explaining the state where the conventional endoscope cannot be inserted into the S-shaped colon.
Figure 34:
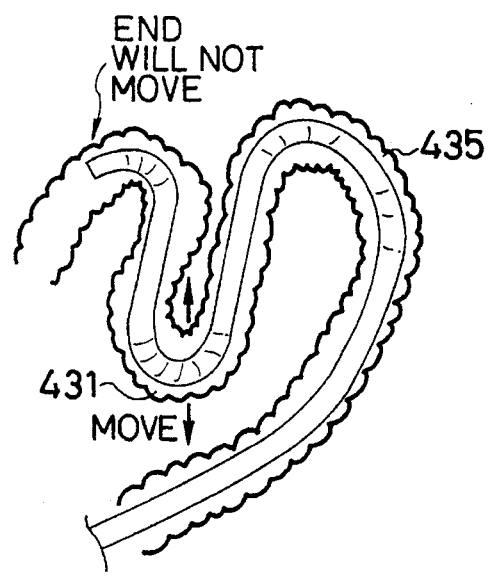
FIG. 34 is an illustration for assistance in explaining the state where the conventional endoscope cannot be inserted into the traverse colon.

FIGS. 33 and 34 show the state where the conventional endoscope cannot be inserted into the large intestine. Since the S-shaped colon 430 and the traverse colon 431 are movable, the flexible pipe 435 is bent largely at the respective positions, with the result that the end of the flexible pipe 401 will not move forward and therefore cannot be inserted.

Figure 35:
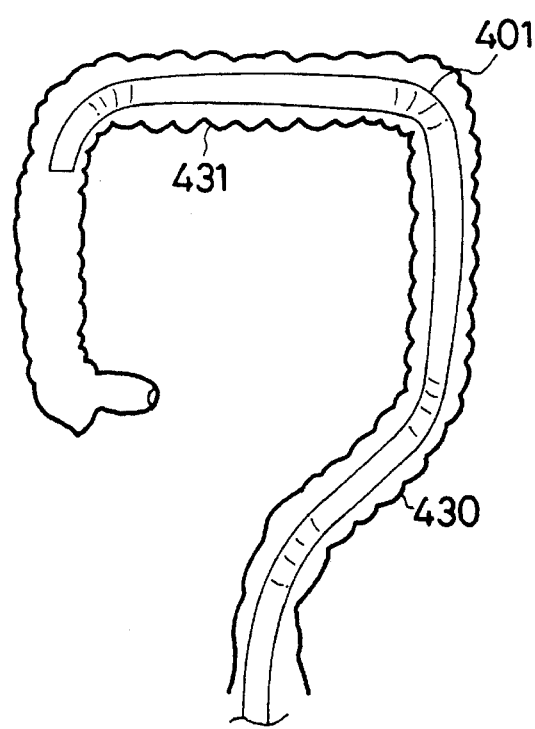
FIG. 35 is an illustration for assistance in explaining the state where the endoscope of the present invention can be inserted into the large intestine.

FIG. 35 shows the shape of the large intestine obtained when the endoscope system of the present embodiment is used for the large intestine examination. In the endoscope of this embodiment, since it is possible to select the segments corresponding to the S-shaped colon 430 and the traverse colon 431 (as shown by the oblique lines in FIG. 35) of the flexible pipe 401 in such a way as not to be flexible, by operating the endoscope system in accordance with the procedure as already explained with reference to FIGS. 23 to 31, the flexible pipe can be inserted easily. Further, when the flexible pipe has been inserted to the position at which the pipe will not be bent, the voltage applied to the segments is released.

Further, in the above description with reference to FIG. 26, although the outermost layer 409 and the innermost layer 414 of the outer elastomer cover 404 of the flexible pipe are formed uniformly, it is possible to divide the outermost layer 409 and the innermost layer 414 into segments, respectively and further to control the flexibility for each segment, in order to further improve the easiness of the flexible pipe insertion.

FIFTH EMBODIMENT

In this embodiment, the flexibility of the flexible pipe is controlled by applying pressure to the outer elastomer cover with the use of fluid (e.g., water, air, etc.) passed therethrough.

Figure 36:
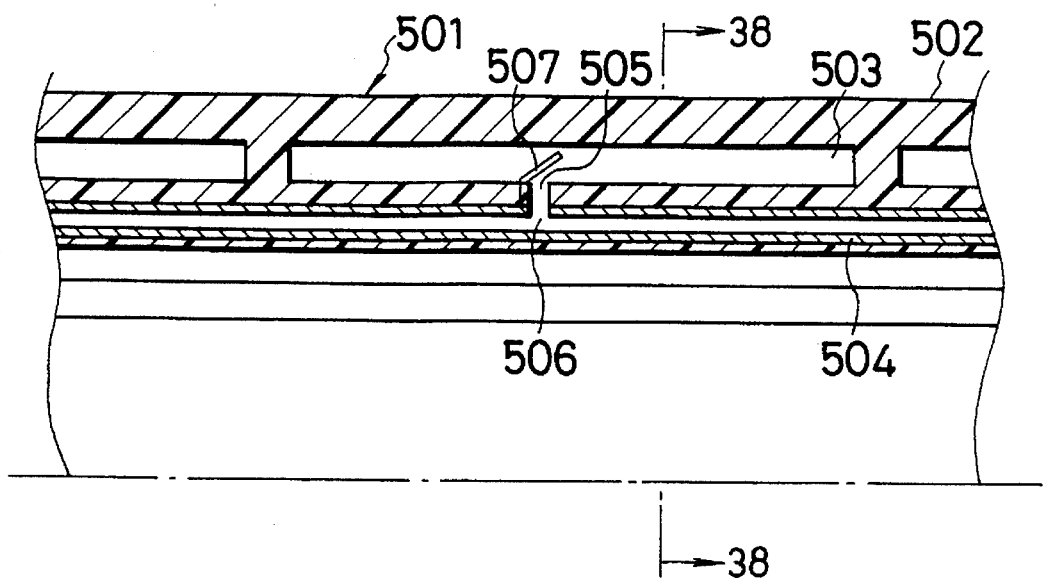
FIG. 36 is an enlarged partial cross-sectional view showing the structure of a fifth embodiment of the flexible pipe of the endoscope system according to the present invention.
Figure 37:
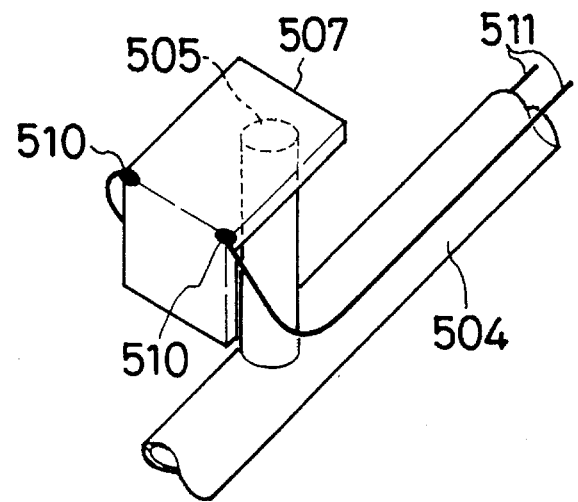
FIG. 37 is a perspective view showing the structure of the valve provided for the flexible pipe shown in FIG. 36.
Figure 38:
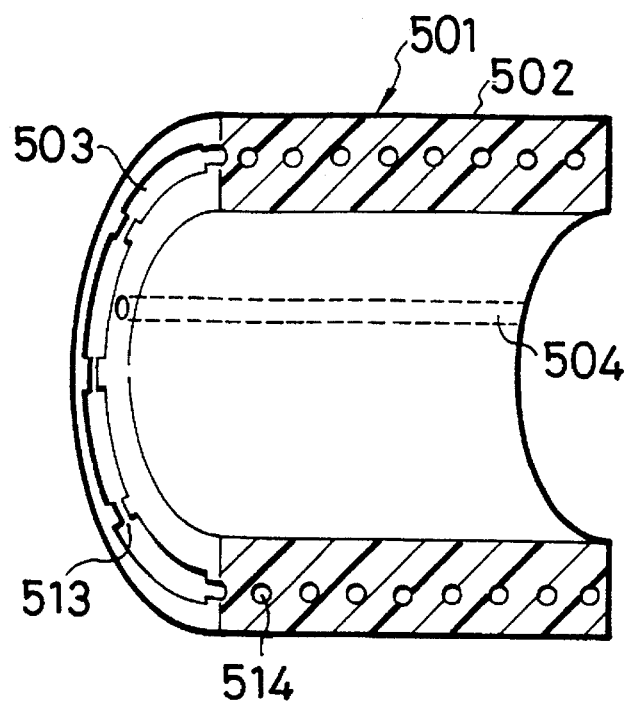
FIG. 38 is a perspective cross-sectional view showing the flexible pipe, taken along the line 38—38 in FIG. 36 and a segment.
Figure 39:
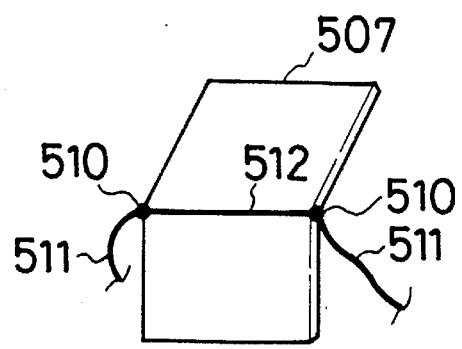
FIG. 39 is an illustration showing the state where a heater is wound at the heating portion of the valve structure.

As shown in FIG. 36, the outer elastomer cover of the flexible pipe 501 is formed with a plurality of air layers or chambers 503. These air layers 503 are divided into segments. Further a tube 504 for flowing fluid such as air or water is provided for each segment. The outer elastomer cover 502 is formed with a hole 505 and the tube 504 is formed with a hole 506. These two holes 505 and 506 are formed at such a position so as to be overlapped with respect to each other. A fluid valve 507 is provided at the hole 505 to control the charge and discharge of the fluid to and from the air layer 503. This fluid valve 507 is formed of a thin film of the shape memory alloy and covered with an insulating substance. As shown in FIG. 37, the fluid valve 507 provided for each segment have two electrodes 510 covered with an insulating substance. The two electrodes 510 are connected to two conductors 511 also covered with an insulating substance, respectively. Therefore, when current is passed through these conductors 511, since the fluid valve 507 is heated and thereby bent at and near the straight portion connected between the two electrodes 510, the hole 505 is closed. To improve the thermal conductivity of the shape memory alloy of the fluid valve 507, it is also preferable to wind a heater 512 covered with an insulating film about the heated portion and to pass current therethrough, as shown in FIG. 39. FIG. 38 is a perspective cross-sectional view taken along the axial direction of the flexible pipe and along the line 38—38 of FIG. 36, in which the cross section at the boundary between the two adjacent segments is depicted. As shown in FIG. 38, partitions 513 are provided in the air layers or chambers 503 of the flexible pipe 501, respectively to prevent the outer elastomer cover 502 from being distorted in the radial direction of the air layers 503. Each of the partitions 513 is formed with a plurality of holes 514 for passing fluid therethrough.

Figure 40:
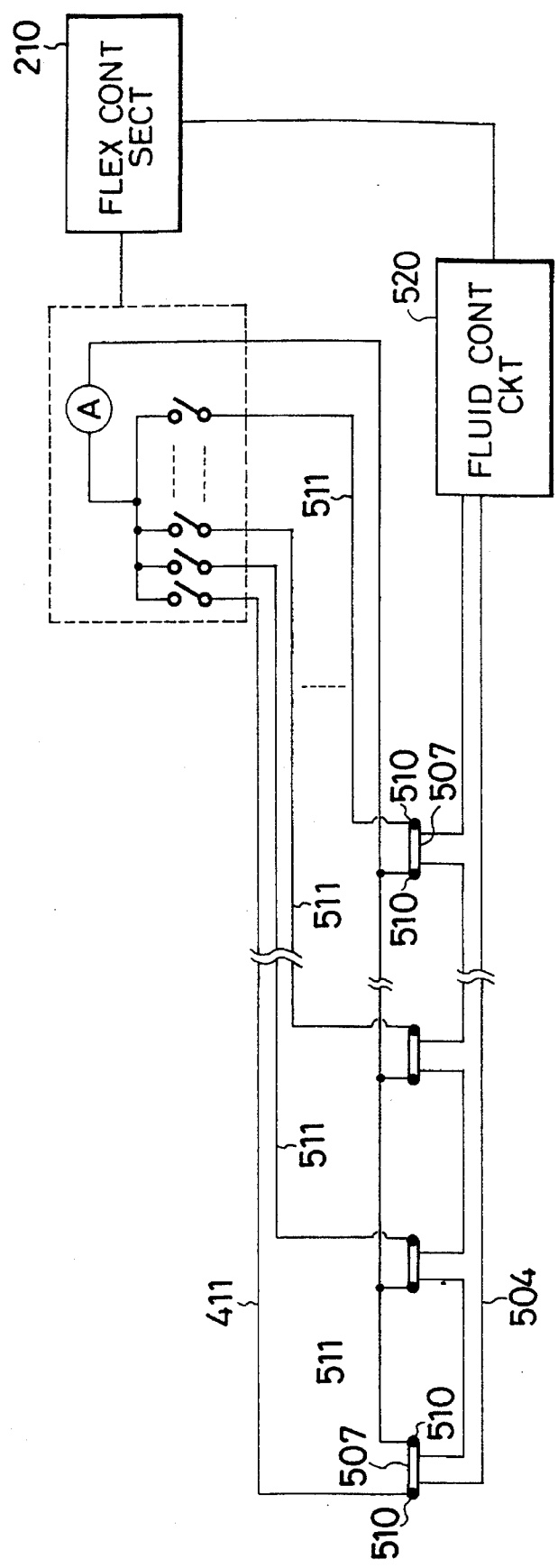
FIG. 40 is a circuit diagram showing a control circuit for controlling the valve shown in FIG. 37.

FIG. 40 shows a control circuit of this embodiment. After fluid has been passed into the respective segments through the tubes 504, only the segments required to be hardened are designated by the operator. Then, only the fluid valves 504 of the designated segments are energized (turned on) and therefore closed. Thereafter, when the fluid is discharged, the fluid remains only in the segments whose fluid valves 504 have been closed, so that only these segments become hard because the chamber is filled with the fluid. To return the hardened segments to the original soft state, the designation of the segments are released. Then, since the fluid valves of the released segments are deenergized (turned off), so that no current flows therethrough. The segments are cooled by the fluid naturally, and therefore the shapes of the fluid valves are returned, so that the fluid valves are open to discharge the fluid. The similar operation is effected to change the segments required to be hardened. The flexibility of the flexible pipe 501 can be controlled as described above. The above-described control is conducted by the flexible pipe flexibility control section 210 and a fluid control circuit 520.

SIXTH EMBODIMENT

In this embodiment, the flexibility of the flexible pipe is controlled by changing the engage rates (gaps) between two adjacent flexes (extensible or retractable band members) constituting the flexible pipe.

In this embodiment, a helical pipe constructed by connecting a plurality of flexes (each of whose both ends are bent) are used as the flexible pipe. The minimum radius of curvature of the helical pipe can be controlled by adjusting the gap distances or intervals between two adjacent flexes. To adjust the gap distances thereof, a tube is provided for each gap and a fluid is passed through this tube.

Figure 41:
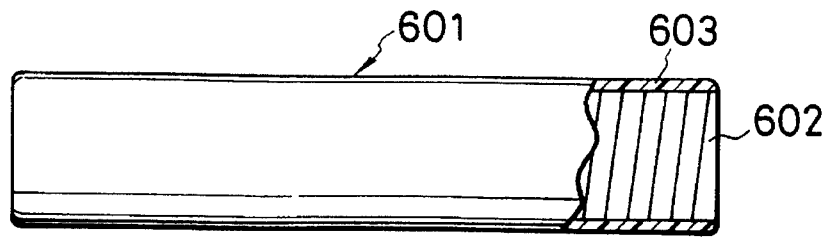
FIG. 41 is a partial cross-sectional view showing a sixth embodiment of the flexible pipe of the endoscope system according to the present invention.

FIG. 41 shows the structure of the flexible pipe 601 of this embodiment, in which the pipe 601 is roughly composed of the helical pipe 602 and an elastic member such as elastomer 608 for covering the helical pipe 602.

Figure 42:
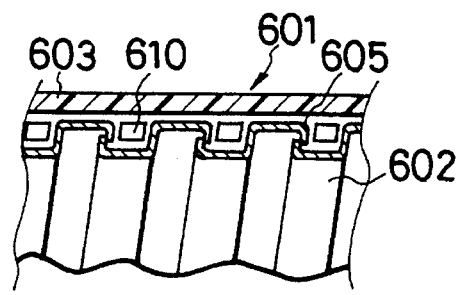
FIG. 42 is an enlarged cross-sectional view showing the bend structure of the helical pipe of the flexible pipe shown in FIG. 41.
Figure 46:
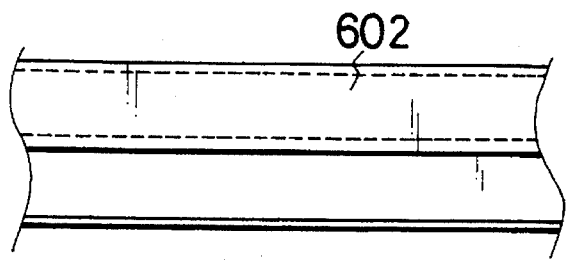
FIG. 46 is a plane view showing the band plate of bend structure shown in FIG. 43.
Figure 47:
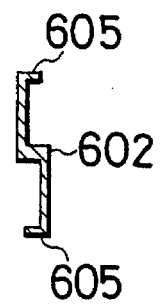
FIG. 47 is a cross-sectional view showing the band plate shown in FIG. 46.

FIG. 42 is an enlarged view showing the bend structure of the helical pipe 602, in which bent portions 605 of the helical pipe 602 and tubes (actuators) 610 for adjusting the gap distances between two adjacent helical pipes 602 are shown. The flexible pipe 601 is formed by a plurality of band plates 602. The both side edge portions of each band plate 602 are bent to form bent portions 605, as depicted in FIGS. 46 and 47,. These bent portions 605 of the band plates 602 are engaged with each other when assembled into a helical shape, as shown in FIG. 42.

Figure 43:
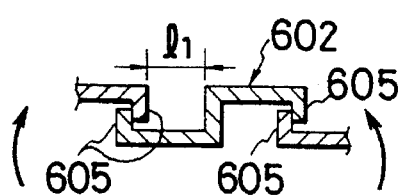
FIG. 43 is an enlarged view showing the bend structure shown in FIG. 42.
Figure 44:
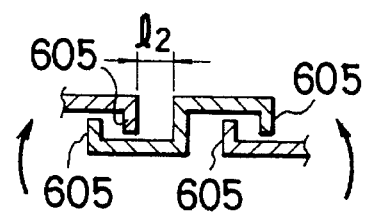
FIG. 44 is an enlarged view showing the state where the gap of the bend structure is reduced.
Figure 45:
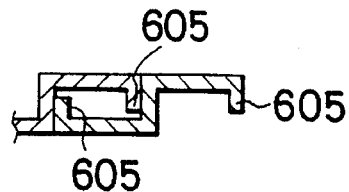
FIG. 45 is an enlarged view showing the state where the gap of the bend structure is further reduced to zero.

The relationship between the gap distance and the minimum radius of curvature of the bent portions 605 will be described hereinbelow with reference to FIGS. 43, 44 and 45. In FIG. 43, the gap distance is designated by $l_1$ when the curvature of the helical pipe 602 is zero (the radius of curvature: $\infty$). Here, when the helical pipe 602 is bent in the arrow direction as shown In FIG. 43, the gap distance changes to $l_2$ as shown in FIG. 44, and therefore $l_1 > l_2$ can be established. That is, the gap distance decreases with increasing curvature (or decreasing radius of curvature) and further reduced to zero (both the bent portions 605 are brought into contact with each other) as shown in FIG. 45. The radius of curvature of the helical pipe 602 in the state as shown in FIG. 45 is referred to as the minimum radius of curvature.

As understood with reference to FIGS. 43, 44 and 45, the minimum radius of curvature of the helical pipe 602 increases with decreasing gap distance $l_1$ obtained in the state of zero curvature (radius of curvature: $\infty$). In other words, the minimum radius of curvature of the helical pipe 602 decreases with increasing gap distance $l_1$ obtained in the state of zero curvature (radius of curvature: $\infty$). In this embodiment, therefore, the tube (actuator) 610 formed of an elastic member is used to adjust the gap distance under remote control. In more detail, when fluid is passed through the tube 610, since the volume of the tube 610 increases, the gap distance is decreased equivalently. On the other hand, when fluid is not passed therethrough, since the volume thereof decreases, the gap distance is increased equivalently. In other words, it is possible to control the minimum radius of curvature of the helical pipe 602 by adjusting the volume of fluid passed through the tube 610 and consequently to change the flexibility of the flexible pipe 601 now under examination.

Figure 48:
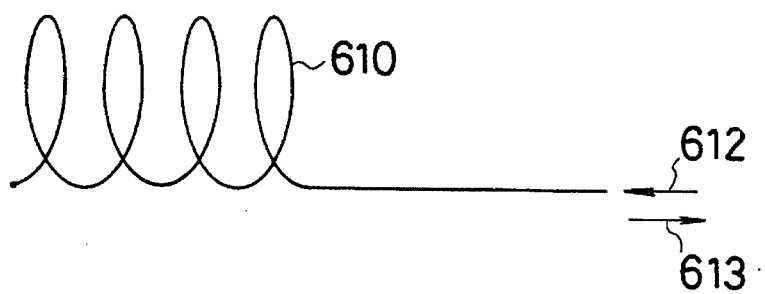
FIG. 48 is an illustration showing the pipe structure inserted between the bent portions shown in FIG. 42.

FIG. 48 shows the structure of the tube 610. In this embodiment, since the flexible pipe 601 is divided into several segments, the tube 610 is arranged into a helical shape along the gap between the bent portions 605 of each segment, as shown in FIG. 48. Further, the fluid (e.g., water, air, etc.) is charged into the tube 610 in an arrow direction 612 and discharged from the tube 610 in an arrow direction 613.

Figure 49:
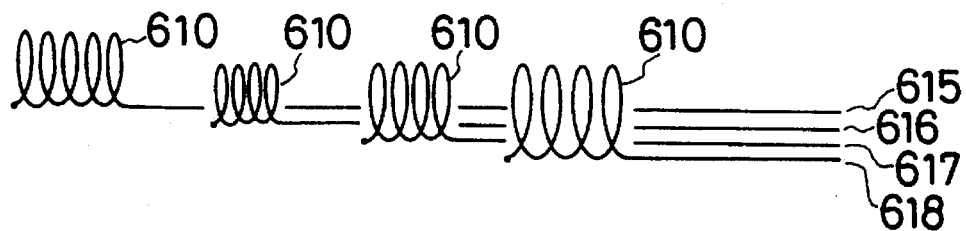
FIG. 49 is an illustration showing the state where the pipe shown in FIG. 48 is provided for each pipe.

FIG. 49 shows all the tubes 610 arranged for the flexible pipe 601, in which the flexible pipe 601 is divided into four segments as shown in FIG. 25, by way of example. Since the volume of the fluid to be charged is independent for each segment, the number of fluid inlet ports 615, 616, 617 and 618 is the same as the number of the segments. Further, the fluid inlet ports can be used in common as the fluid outlet ports.

The method of using the flexible pipe 601 of this embodiment in the actual examination will be described hereinbelow. The endoscope system is composed of the endoscope section 203 and the main frame unit 202, as shown in FIG. 7. Further, the main frame unit 202 is composed of the central control section 207, the flexible pipe flexibility control section 210, the flexible pipe flexibility pattern data base 209, and the image display control section 208. The volumes of fluid to be fed and the segments to be charged are controlled and selected by the flexible pipe flexibility control section 210. In more detail, the operator recognizes the shape of the flexible pipe 601 in the interior of the body cavity on the basis of the X-ray fluoroscopic image or estimates the same on the basis of the image obtained by the flexible pipe flexibility pattern data base 209, and decides the flexibility pattern to be now adopted. The information related to the decided flexibility pattern is transmitted to the flexible pipe flexibility control section 210 via the central control section 207 to change the flexibility of the flexible pipe 601. The fluid is charged to the segments whose flexibility are required to be decreased (non-flexible state), so that the gaps between the flexes are burled by the tubes 610 to increase the minimum radius of curvature of the helical pipe 602. On the other hand, the fluid is discharged from the segments whose flexibility is required to be increased (flexible state), so that the gaps between the flexes are increased to decrease the minimum radius of curvature of the helical pipe 602, irrespective of the presence of the tubes 610. As described above, it is possible to change the flexibility of the flexible pipe 601 and therefore to improve the easiness of insertion of the flexible pipe 601.

SEVENTH EMBODIMENT

Figure 50:
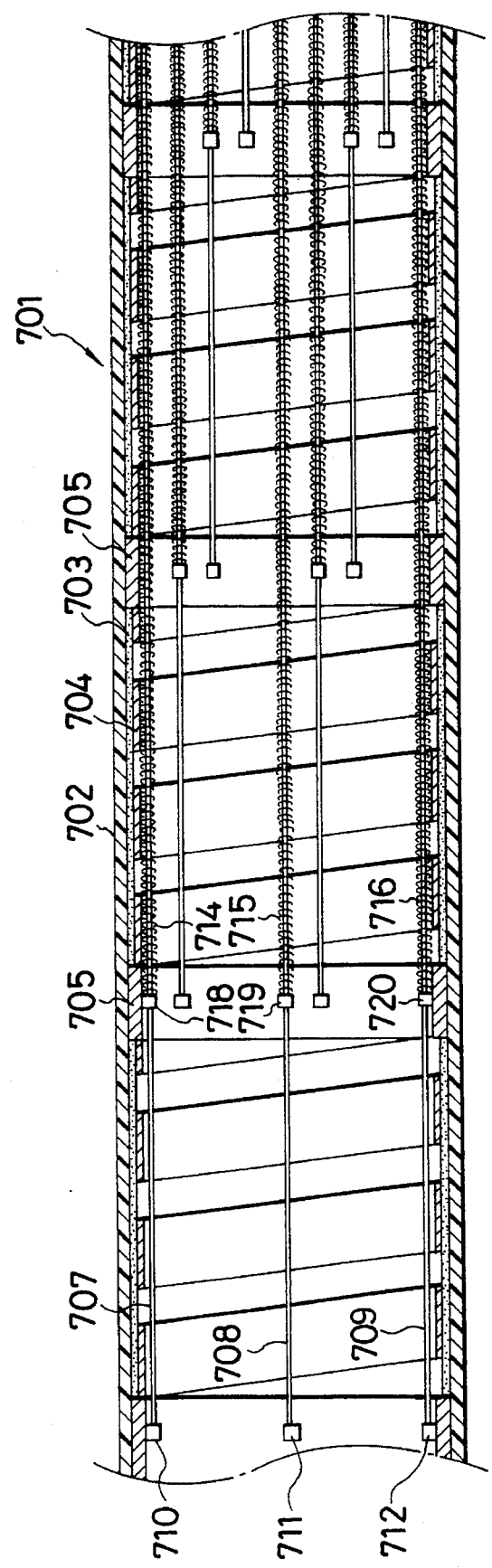
FIG. 50 is a longitudinal cross-sectional view showing a seventh embodiment of the flexible pipe of the endoscope system according to the present invention.
Figure 53:
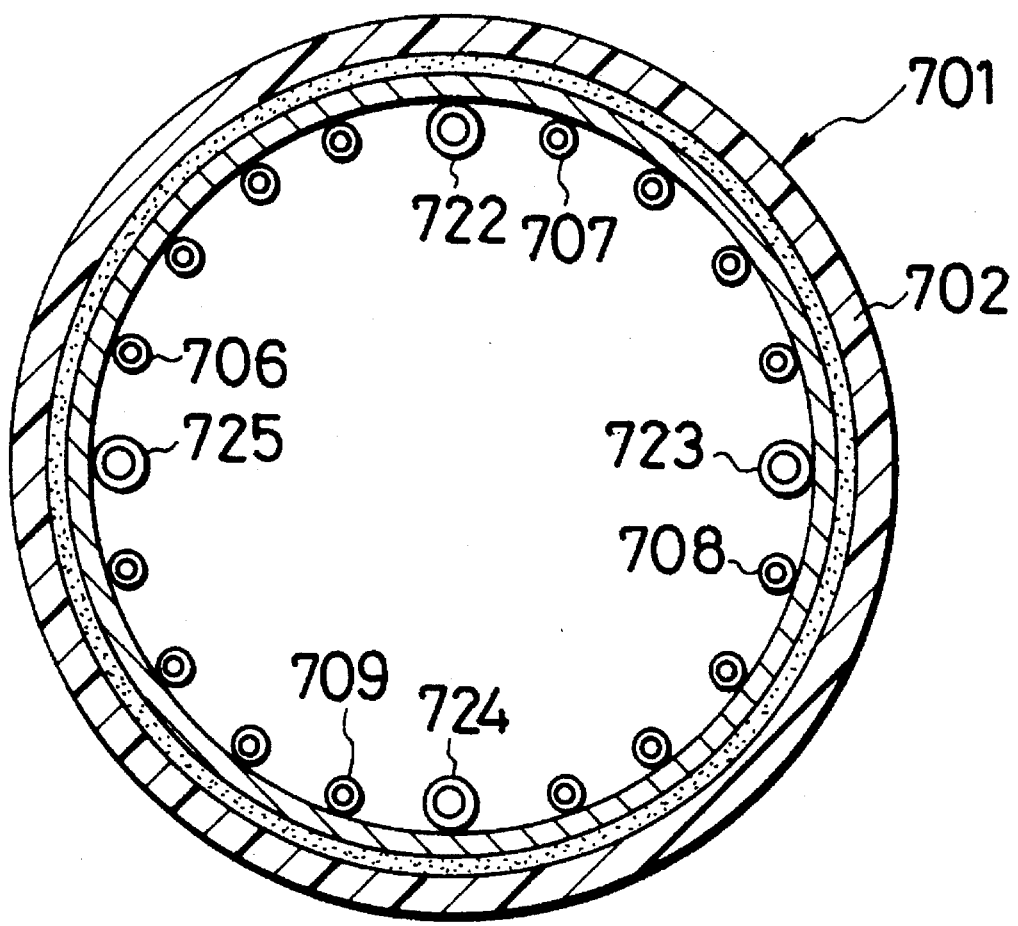
FIG. 53 is a transverse cross-sectional view showing the structure of the flexible pipe shown in FIG. 50.

In this embodiment, wires are arranged in the flexible pipe, and the flexibility of the flexible pipe is changed by controlling the tension of the wires. FIG. 50 is a longitudinal cross-sectional view showing the flexible pipe 701 and FIG. 53 is a transverse cross-sectional view showing the same. In these drawings, the outer circumferential surface of the flexible pipe 701 is covered with an outer elastomer cover 702. Within this outer elastomer cover 702, a metallic mesh-shaped braid 703 and a metallic helical pipe 704 are arranged. The helical pipe 704 and the braid 703 are divided into segments by use of holding rings 705, and further fixed to each other at this holding rings 705, respectively. Wires 707 to 709 are fixed to the holding rings 705 with fixture members 710 to 712, respectively. Each of the wires is exposed at the segment at which a tension can be applied, but covered with a sheath (formed by winding a metallic wire helically) 714 to 716 at the holding ring 705 positioned at the boundary between the two segments. The end of each of the sheaths 714 to 716 is fixed to one of the holding rings 705 with one of fixture members 718 to 720. Each of the wires 707 to 709 can be moved freely at each of the sheath fixture members 718 to 720. Four wires are arranged for each segment at angular intervals of 90 degrees about the central axis of the endoscope, as shown by the reference numerals 706 to 709 in FIG. 53. FIG. 53 shows the state where the flexible pipe 701 is divided into four segments. Further, in FIG. 53, four angle wires 722 to 725 for bending the endoscope end are shown.

Figure 51:
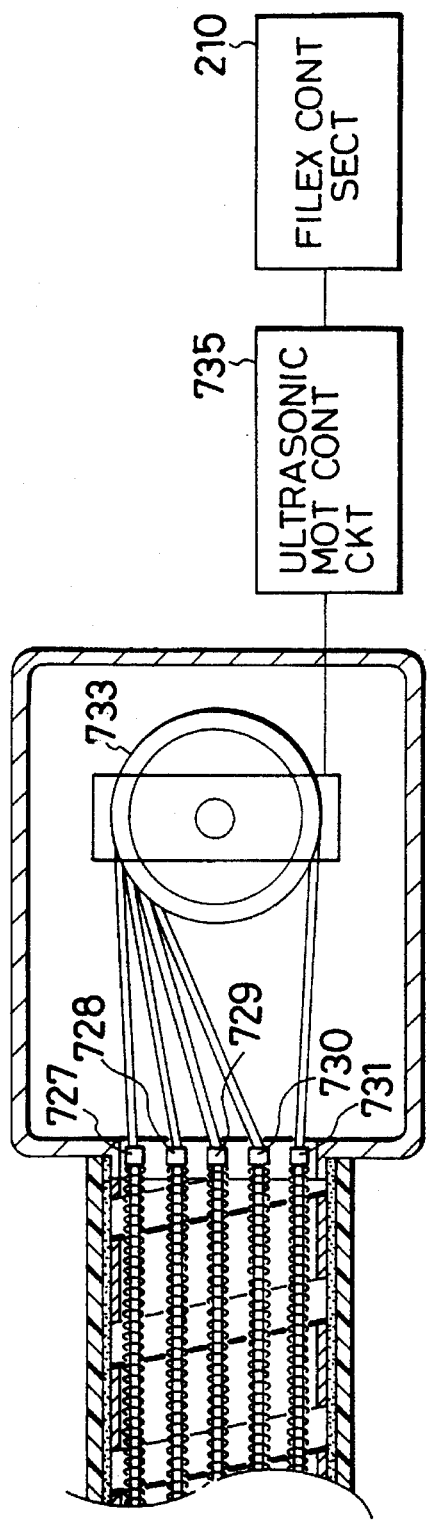
FIG. 51 is a longitudinal cross-sectional view showing the grip portion of the flexible pipe shown in FIG. 50.
Figure 52:
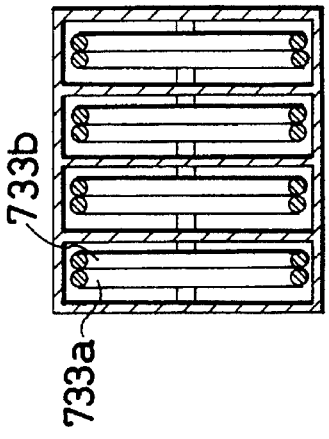
FIG. 52 is a transverse cross-sectional view showing the grip portion of the flexible pipe shown in FIG. 51.

FIG. 51 shows the grip portion of the endoscope of this embodiment. The wires 707 to 709 extending from the segments are passed through sheath fixture members 727 to 731 and then wound up around wire roll-up pulleys 733, respectively. The end of each of the wires is fixed to each of the pulleys 733. Two pulleys 733a and 733b are provided for each segment, and rotate in two opposite directions by two ultrasonic motors disposed within the two pulleys 733, respectively. Two of the four wires for one segment are wound around one 733a of the two pulleys 733 and the remaining two of the four wires are wound around the other 733b of the two pulleys 733.

The flexibility of the flexible pipe can be controlled as follows: When the flexible pipe flexibility control section 210 of the main frame unit 202 outputs a command for selecting a segment required to be hardened, an ultrasonic motor control circuit 735 drives the ultrasonic motors corresponding to the segment, so that the pulleys 333 are rotated to apply a tension to the four wires connected to the segment to be hardened. To reduce the applied tension applied to the wires, the ultrasonic motors are rotated in the reverse direction. The number of segments to be hardened and the number of segments to be softened can be determined freely.

In the above description, although four wires are used for each segment by way of example, it is of course possible to use three wires. Further, it is also possible to use three or four wires in common for the respective segments and then to divid them for each segment, respectively. Further, the number of segments to be divided is not limited to only four.

EIGHTH EMBODIMENT

Figure 54:
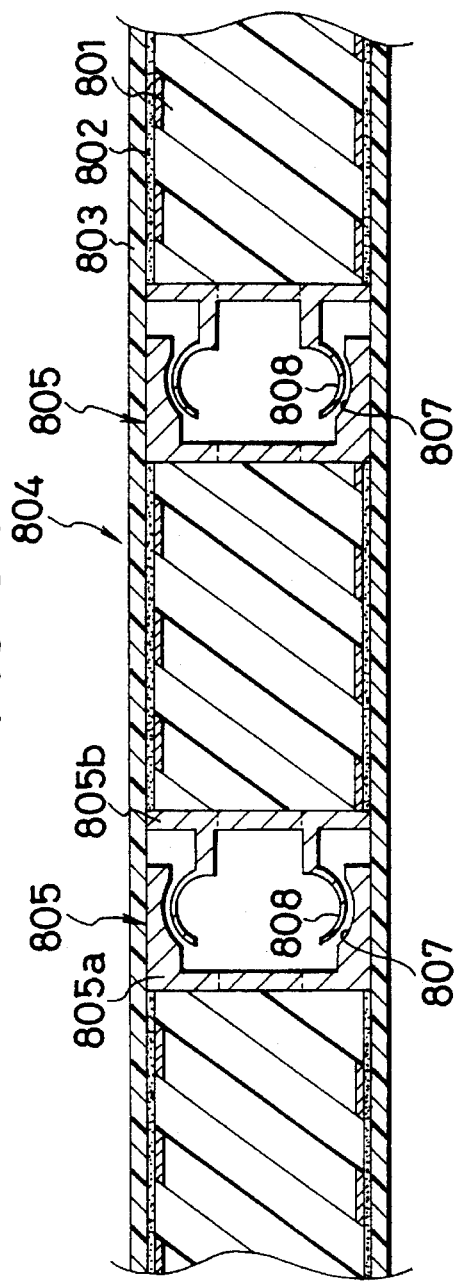
FIG. 54 is a longitudinal cross-sectional view showing an eighth embodiment of the flexible pipe of the endoscope system according to the present invention.
Figure 55:
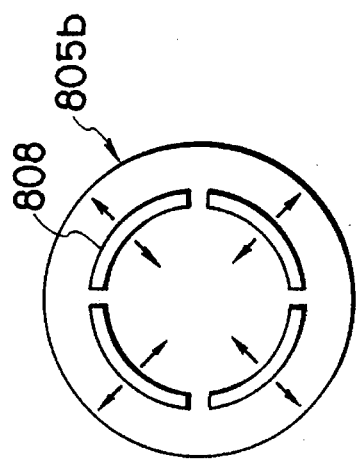
FIG. 55 is a front view showing the joint provided for the flexible pipe shown in FIG. 54.

In this embodiment, the flexible pipe is divided into several segments, and the movability of joints connecting these segments is changed to control the flexibility of the flexible pipe. FIG. 54 is a cross-sectional view showing the flexible pipe of the endoscope of this embodiment, in which a flexible pipe 804 is composed of flexes 801, a braid 802 and an outer elastomer cover 803, and is divided into several segments by joint portions 805, respectively. The joint portion 805 is constructed as follows: an outer joint member 805a and an inner joint member 805b are connected to both the flex 801 (in the axial direction) and the braid 802 (in the radial direction). The inner concave spherical surface 807 of the outer joint member 805a is engaged with the outer convex spherical surface 808 of the inner joint member 805b, so that the two adjacent segments can be moved along both the spherical contact surfaces and thereby bendable. Therefore, when the contact resistance between the two joint members 805a and 805b changes, the flexibility of the flexible pipe can be controlled. The joint member 805a is formed so as to be rigid to some extent; on the other hand, the joint member 805b is formed into divided structure so as to be deformable in the radial direction thereof, as shown in FIG. 55. To increase the contact resistance between the two joint members 805a and 805b, the contact surface can be coated by elastomer, for instance. The movability of the joint portions can be controlled by deforming the convex spherical portion 808 of the joint member 805b so that the contact resistance can be changed as follows:

(1) Method of using doughnut-shaped tube

Figure 56:
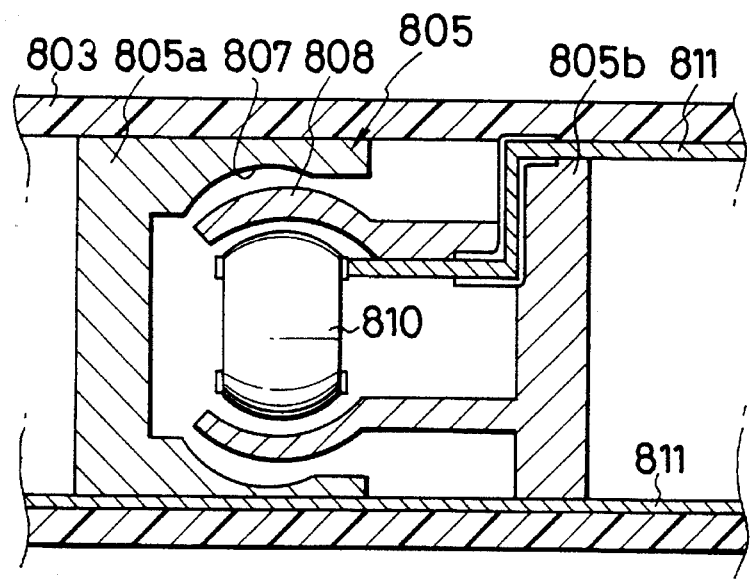
FIG. 56 is a cross-sectional view showing the doughnut-shaped pipe provided for the joint shown in FIG. 55.
Figure 57:
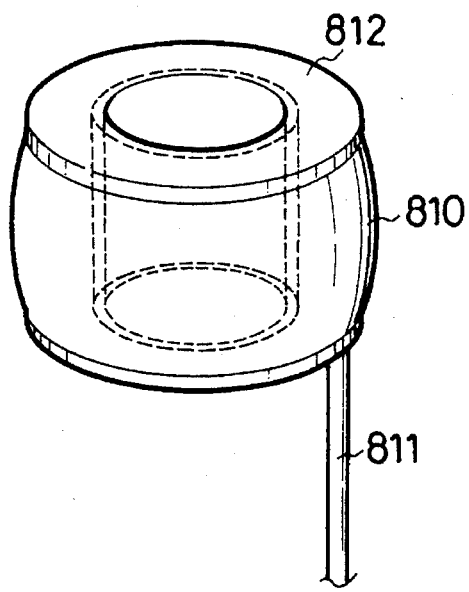
FIG. 57 is a perspective view showing the doughnut-shaped pipe shown in FIG. 56.
Figure 58:
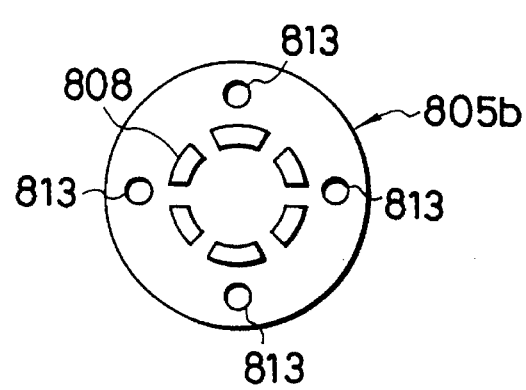
FIG. 58 is a front view showing the joint shown in FIG. 56.

As shown in FIG. 56, a doughnut-shaped tube 810 is disposed within the inner circumferential surface of the convex spherical portion 808 of the joint member 805b, and fluid (e.g., air, water, etc.) is passed through a fluid tube 811 to expand the doughnut-shaped tube 810 in the radial direction, with the result that the convex spherical surface 808 of the joint member 805b can be deformed. As shown in FIG. 57, a metallic cylinder is fitted to the central hole of the doughnut-shaped tube 810 and further two annular plates 812 are attached to both upper and lower sides thereof, so that the doughnut-shaped tube 810 can be expanded only in the outward radial direction when fluid is passed therethrough. Further, a hole 813 is formed in the lower surface of the doughnut-shaped tube 810 to fit a fluid tube 811 for charging fluid into the doughnut-shaped tube 810 thereto. As shown in FIG. 58, the fluid tubes 811 are arranged at different angular positions of the doughnut-shaped tubes 810 of the respective segments.

Figure 59:
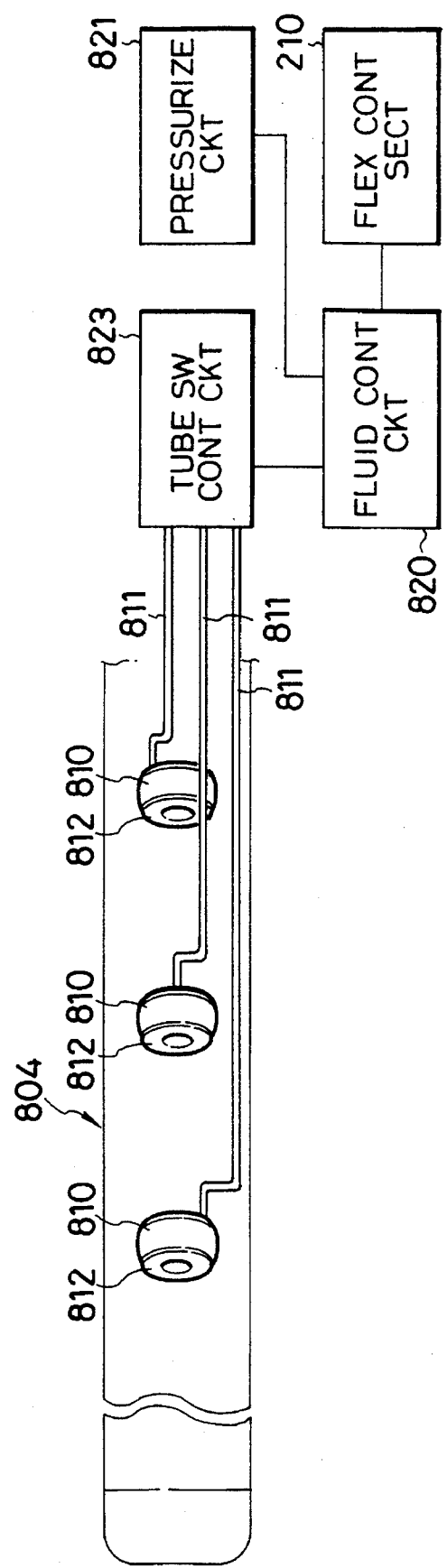
FIG. 59 is a block diagram showing a control circuit for controlling the doughnut-shaped pipe provided for each segment of the flexible pipe shown in FIG. 54.

FIG. 59 shows the method of charging fluid into the doughnut-shaped tubes 810. On the basis of a command applied by the flexible pipe flexibility control section 210, a fluid control circuit 820 controls the fluid pressurized by a pressurizing circuit 821, and further controls a tube passage switch control circuit 823, so that the tube passages can be switched and thereby the pressurized fluid can be charged only into the doughnut-shape tube 810 required to be expanded.

(2) Method of using specific elastomer

Figure 60:
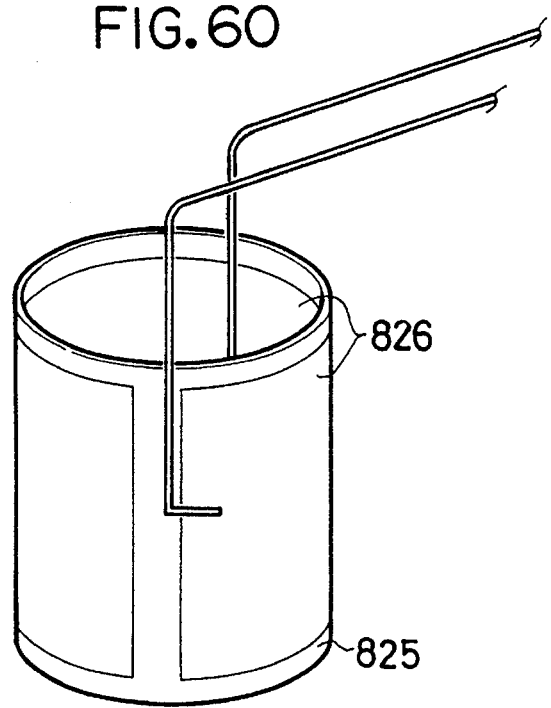
FIG. 60 is a perspective view showing a specific elastomer provided for the joint portion of the flexible pipe shown in FIG. 54.

As shown in FIG. 60, a specific elastomer 825 is used as the outer elastomer cover 803 of the flexible tube 804. In this elastomer 825, the hardness thereof changes according to voltage applied between two electrodes 826 attached to both inner and outer circumferential surfaces of the elastomer 825.

Figure 61:
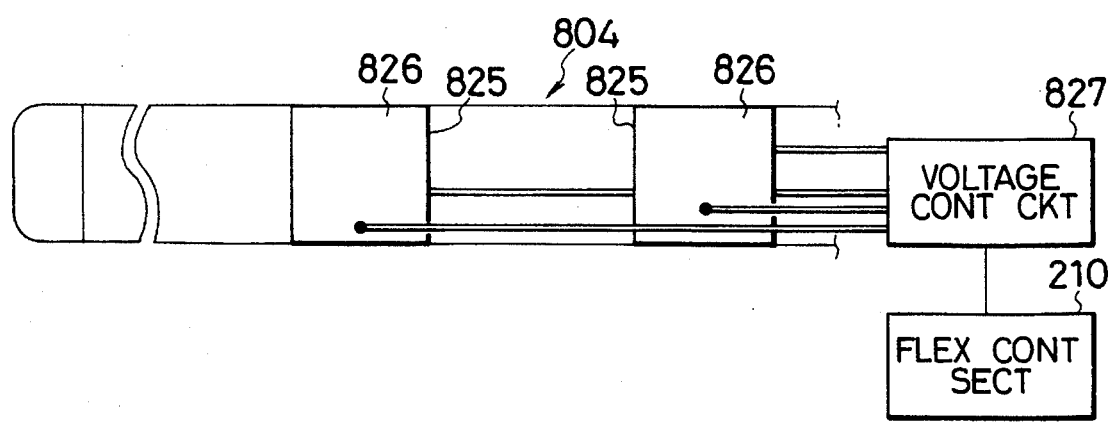
FIG. 61 is a block diagram showing a circuit for controlling the specific elastomer shown in FIG. 60.

As shown in FIG. 61, on the basis of a command of the flexible pipe flexibility control section 210, a voltage control circuit 827 controls the voltage applied between the two electrodes 826, so that the hardness of the specific elastomer 825 disposed at the joint portion can be changed. In other words, the flexibility of the joint portions can be controlled through the specific elastomer 825.

(3) Method of using shape memory alloy

Figure 62:
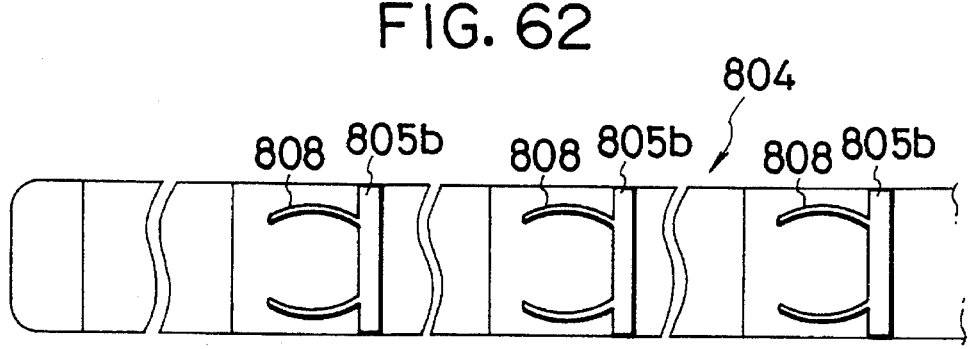
FIG. 62 is an illustration showing the state where the joints formed of the shape memory alloy are provided for the flexible pipe shown in FIG. 54.
Figure 63:
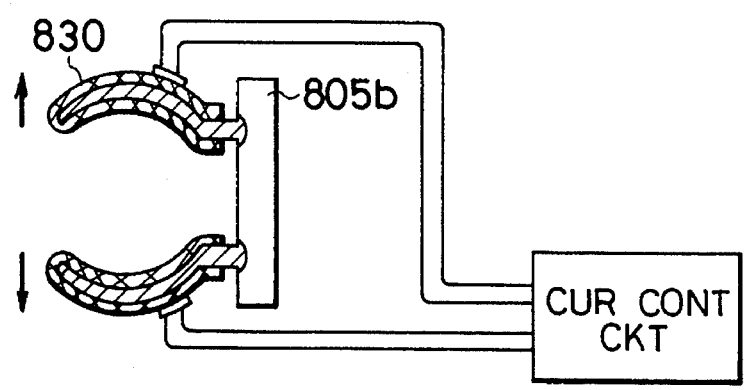
FIG. 63 is an illustration showing the state where the shape memory alloy shown in FIG. 62 is covered by a heater.
Figure 64:
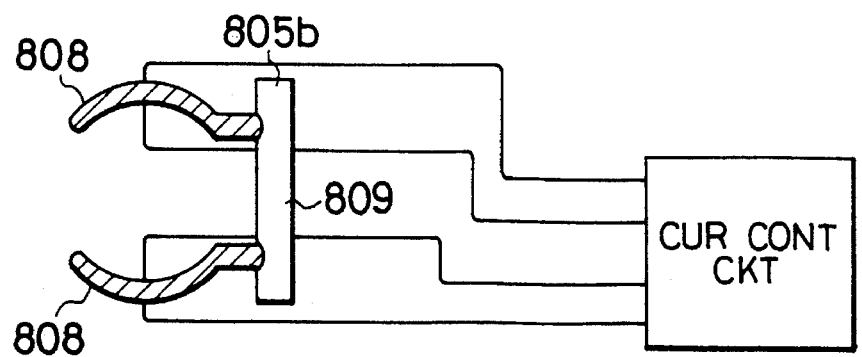
FIG. 64 is a circuit diagram showing a circuit for passing direct current through the shape memory alloy shown in FIG. 62.

The joint members 805b of the flexible pipe 804 are formed of the shape memory alloy. FIG. 62 shows the flexible pipe 804 of joint structure. The convex spherical portion 808 of the joint member 805b is formed of the shape memory alloy. When current is passed through the shape memory alloy to heat the convex spherical portion 808, the convex spherical portion 808 can be deformed in the radial direction, so that the contact resistance of the joint portion can be changed. In FIG. 63, the joint member 805b is covered with a elastomer heater 830, and current is passed therethrough to heat the joint. In the elastomer heater 830, heat generating resistance wire is disposed between two sheets of elastomer. Further, as shown in FIG. 64, it is also possible to arrange conductor on the convex spherical portions 808 of the joint member 805b, and current is passed therethrough to heat the joint. In this method, although the convex spherical portion 808 must be insulated from a joint base 809, the heat efficiency is relatively high.

As described above, since the flexible pipe 804 is divided into several segment portions 805, and further the movability of the joint portions 805 can be controlled, it is possible to change the flexibility of the flexible pipe 804.

NINTH EMBODIMENT

In this embodiment, a shape memory alloy wire is formed integral with the outer cover of the flexible pipe. That is, a spring made of shape memory alloy is embedded in and formed integral with the outermost elastic layer of the flexible pipe. The flexibility of the flexible pipe is controlled on the basis of the shape memory characteristic of the shape memory alloy. The shape of the shape memory alloy can be changed when heated externally, or internally by heat generated due to electric resistance of the alloy by directly passing current through the alloy itself. Further, the shape memory alloy is provided with characteristics similar to the elasticity of elastomer (referred to as superelasticity). In more detail, when the alloy is deformed by a force within the superelastic range, the alloy returns to the original shape after having been released from the force.

Figure 65:
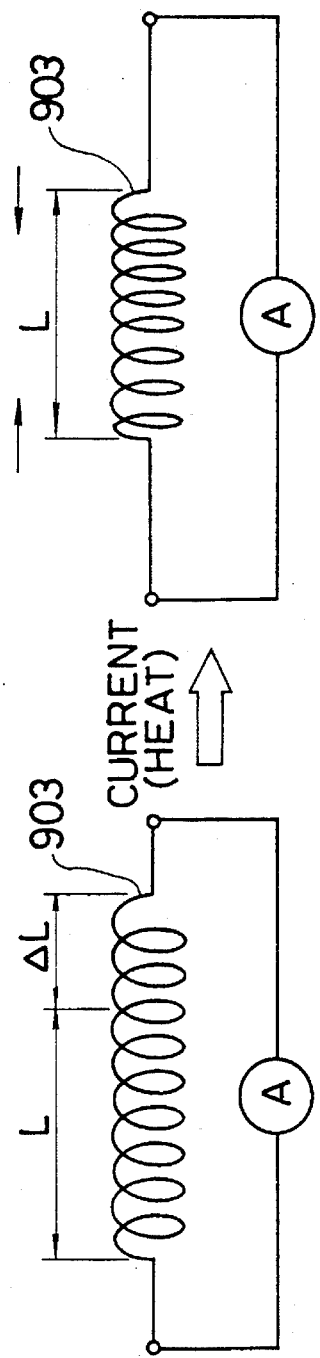
FIG. 65 is an illustration for assistance in explaining the shape memory characteristics of the shape memory alloy provided for a ninth embodiment of the flexible pipe of the endoscope system according to the present invention.

FIG. 65 is an illustration for assistance in explaining the shape memory characteristics of the shape memory alloy, in which the shape thereof is returned to the original shape at a temperature higher than a predetermined temperature. In FIG. 65, the length of a shape memory alloy 903 is first deformed from L to L+$\Delta$L. However, when the alloy is heated beyond a predetermined deformation temperature, the length of the alloy L+$\Delta$L returns to the original length L. To heat the alloy, wire is directly wound around the shape memory alloy and current is passed therethrough.

Figure 66:
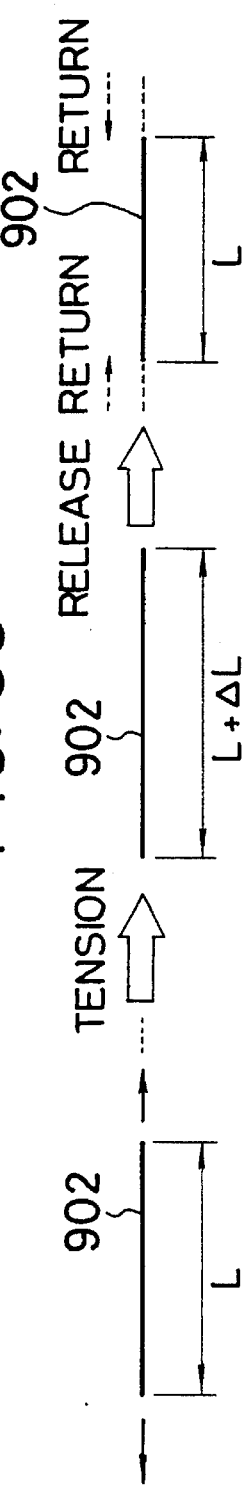
FIG. 66 is an illustration for assistance in explaining the superelasticity of the shape memory alloy provided for the ninth embodiment of the flexible pipe according to the present invention.

FIG. 66 is an illustration for assistance in explaining the superelasticity of the shape memory alloy. In FIG. 66, when a shape memory alloy wire 902 with a length L is lengthened to a length L+$\Delta$L by a force, the alloy wire can be returned naturally to the original length L, as far as the deformation is made within the superelasticity range.

Figure 67:
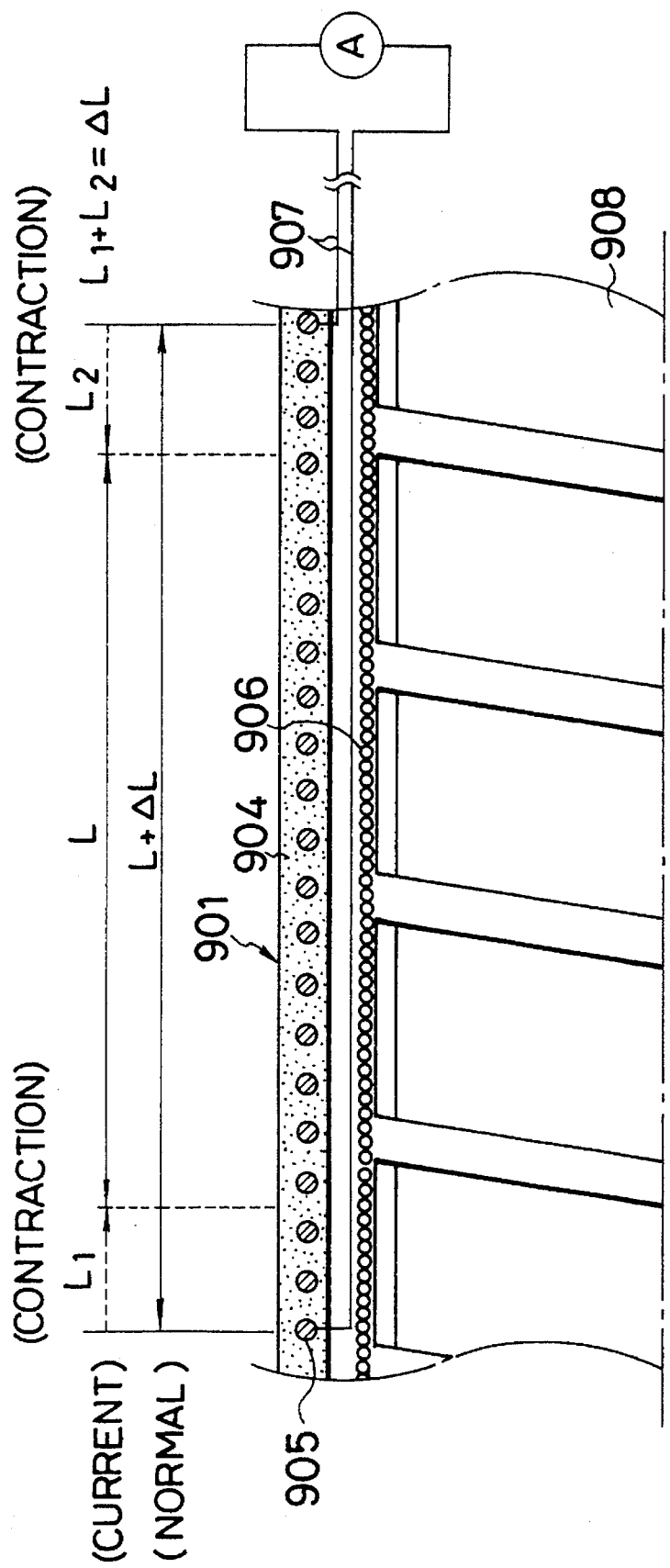
FIG. 67 is a cross-sectional view showing the ninth embodiment of the flexible pipe according to the present invention.

FIG. 67 is a cross-sectional view showing the flexible pipe of the present embodiment. In this embodiment, the shape memory alloy wire is once formed into a helical shape (referred to as shape memory spring, hereinafter) 905 and then heat-treated so that the shape thereof can be returned to the original shape at temperature higher than a predetermined value. The formed shape memory spring 905 is molded integral with the outer cover 904 of the flexible pipe 901, and further connected to electric conductors 907 to directly pass current through the shape memory spring 905 for heat generation. The electric conductors 907 are connected to the flexible pipe flexibility control section 210 of the main frame unit 202 being passed through a hollow portion of the flexible pipe 901. Here, the shape memory spring 905 is molded together with the elastic material of the outer cover 904, under condition that the spring 905 with an original length L is lengthened to another length L+$\Delta$L. Under these conditions, when the shape memory spring 905 is heated by current passed therethrough, since the spring 905 is shortened by a length $\Delta$L, the outer cover 904 is also shortened together with the spring 905. Further, in FIG. 67, the outer cover 904 molded together with the shape memory spring 905 is formed outside the flexes 908 covered with a braid 906.

Figure 68:
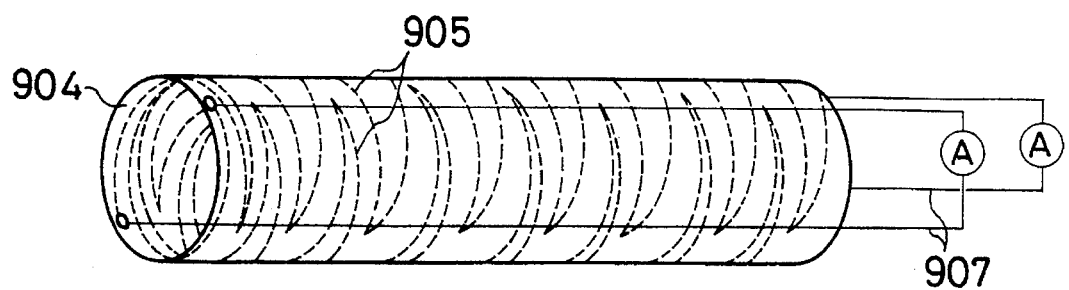
FIG. 68 is an illustration showing a modification of the shape memory alloy provided for the ninth embodiment of the flexible pipe.
Figure 69:
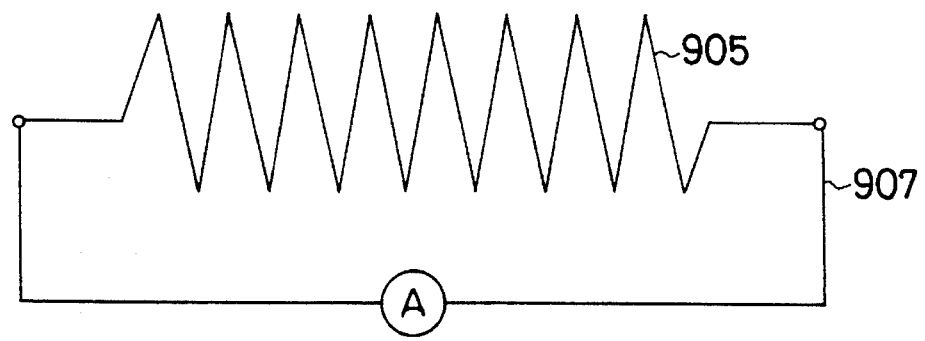
FIG. 69 is a circuit diagram showing a circuit connected to the shape memory alloy shown in FIG. 68.

FIG. 68 shows another method of arranging the shape memory spring 905 in the elastic material of the outer cover 904. In this embodiment, two shape memory alloy wires are formed into a wave-shape spring 905, respectively along the inner circumferential surface of the outer cover 904 in such a way that two springs are arranged for each segment by engaging the respective crests with the respective troughs of the two springs 905. The shape memory springs 905 are then heat-treated so that the shape thereof can be returned to the original shape at temperature higher than a predetermined value. The formed shape memory springs 905 are molded integral with the outer cover 904 of the flexible pipe 901, and further connected to electric conductors 907 to pass current directly through the shape memory springs 905 for heat generation. The electric conductors 907 are connected to the flexible pipe flexibility control section 210 of the main frame unit 202 being passed through a hollow portion of the flexible pipe 901. Here, the shape memory springs 905 are molded together with the elastic material of the outer cover 904, under condition that the springs 905 with an original length L are lengthened to another length L+$\Delta$L. Under these conditions, when the shape memory springs 905 are heated by current passed therethrough, since the springs 905 are shortened by a length $\Delta$L, the outer cover 904 is also shortened together with the spring 905. FIG. 69 shows schematically the wiring method of the shape memory springs 905.

Figure 70:
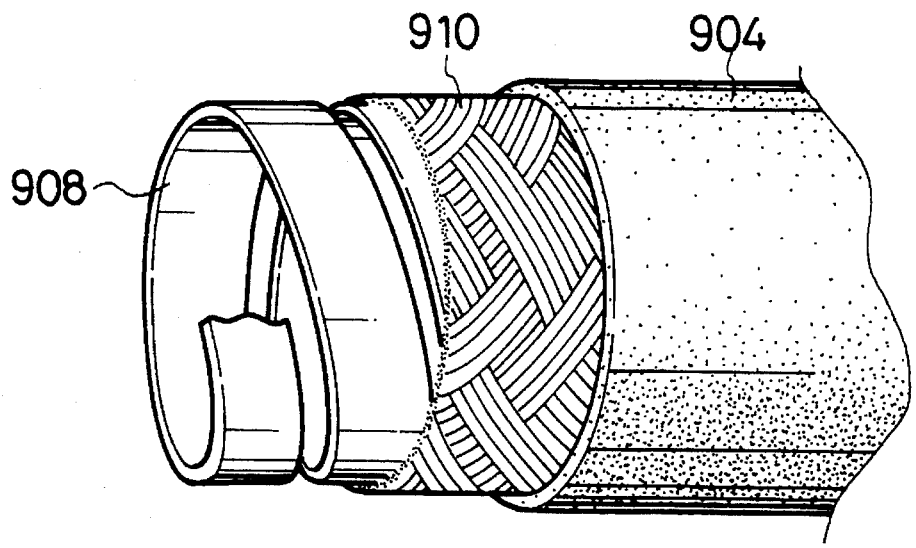
FIG. 70 is an enlarged broken view showing a modification of the ninth embodiment of the flexible pipe.
Figure 71:
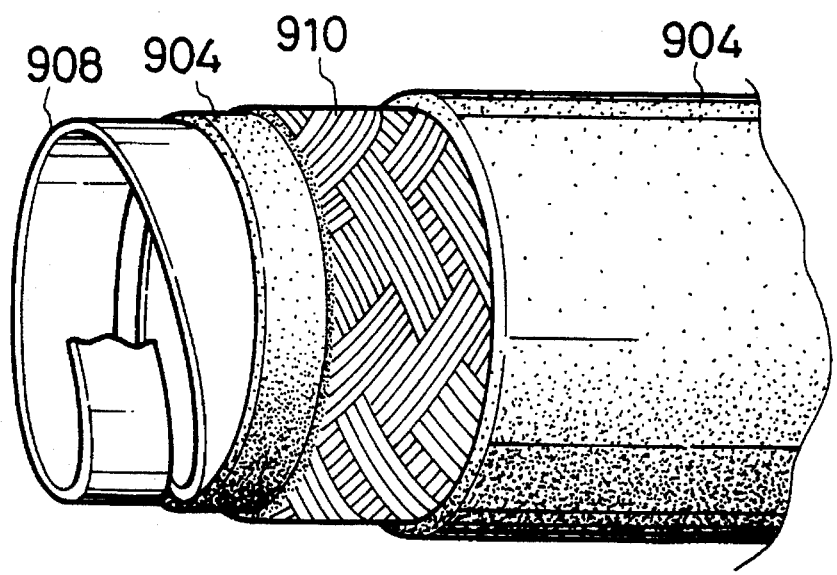
FIG. 71 is an enlarged broken view showing another modification of the ninth embodiment of the flexible pipe.

Further, in order to increase the returning force of the flexible pipe to the original shape, it is also possible to interpose a mesh-shaped braid 910 braided by the shape memory alloy of superelasticity between the outer cover 904 and the flexes 908 of the flexible pipe, as shown in FIG. 70 or between two outer covers 904, as shown in FIG. 71, in such a way that the mesh-shaped braid 910 can follow the deformation of the flexible pipe 901.

Figure 75:
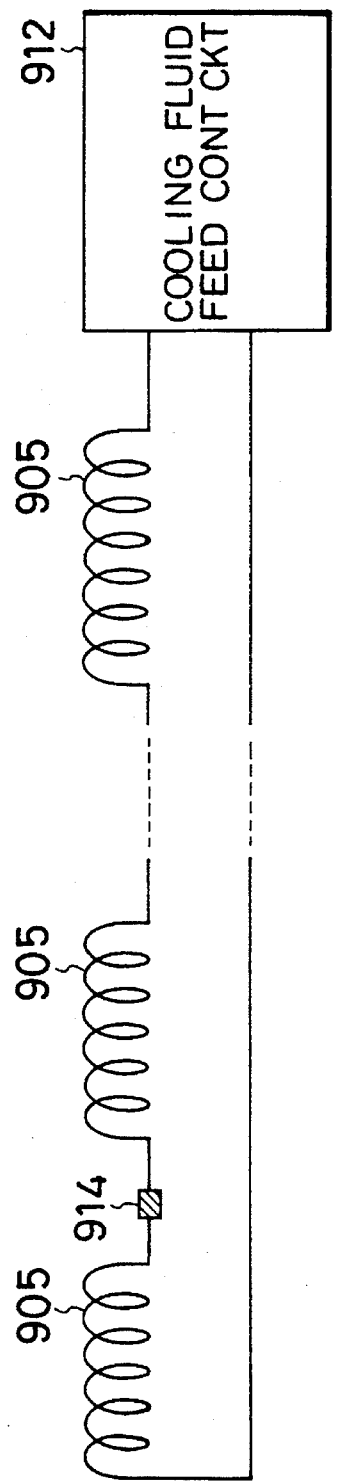
FIG. 75 is an illustration showing a modification of tile shape memory alloy shown in FIG. 74.

In this embodiment, the heated shape memory spring is cooled by a cooling medium, by the method as shown in FIGS. 72 and 73. In this method, the wire of the shape memory spring is formed into a tubular shape and further wound into a helical shape. A cooling medium such as cool air, water or oil is passed through the inner hollow portion of the tubular wire 905 to cool the heated shape memory alloy. Here, the passages for flowing the cooling medium to the shape memory springs are divided for each segment, and controlled by a cooling medium supply control circuit 912 provided in the main frame unit 202, as shown in FIG. 74. Further, as far as the shape memory springs for the respective segments are insulated from each other, it is possible to use only a single cooling medium supply passage, as shown in FIG. 75. In FIG. 75, the respective shape memory springs 905 are insulated by insulating tubes 914, respectively.

Figure 76:
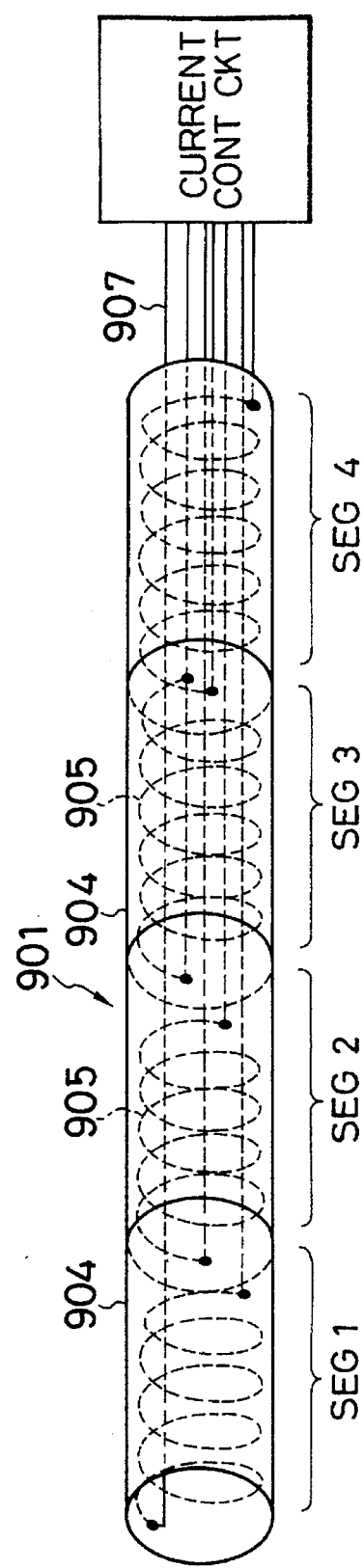
FIG. 76 is an illustration showing another example in which the flexible pipe shown in FIG. 67 is divided for each segment.

The outer cover 904 constructed as described above is divided into several segments, and further connected to each other as an outer cover 904 of the single flexible pipe 901, as shown in FIG. 76. The lengths of the respective segments are determined freely on the basis of the clinical requirements. In this case, since the segments are provided with electric wiring routes 907, respectively, it is possible to control only a single segment or a plurality of segments simultaneously. Accordingly, even when an insertion force cannot be transmitted to the endoscope because the endoscope is deformed at two or more positions in the body cavity, it is possible to insert the endoscope smoothly without deforming the endoscope.

Figure 77:
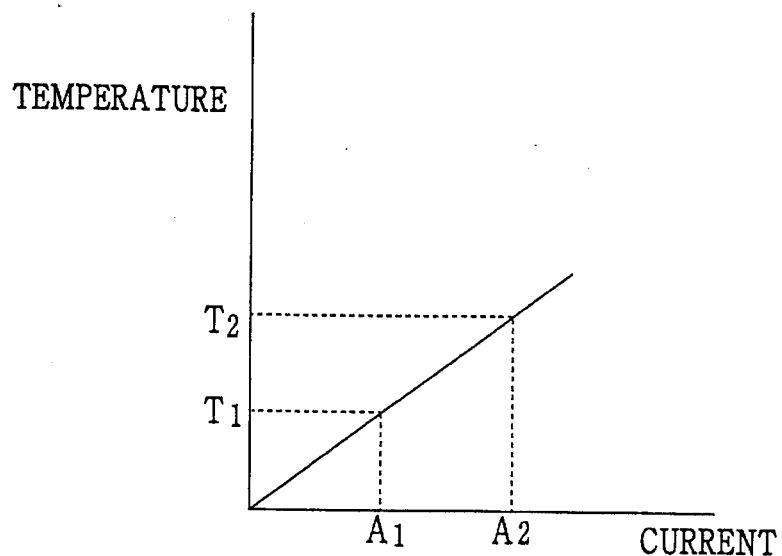
FIG. 77 is a graph showing that deformation starting temperatures are different from each other when the compositions of the shape memory alloys are different from each other.

Besides, the compositions of the shape memory alloys used for the flexible pipe may be different from each other about each segment. In this case, it is possible to control the flexibility by making use of the differences in heat produced by passing current and the differences in deformation starting temperature of the shape memory alloys. FIG. 77 is a graph showing that the deformation starting temperatures of the shape memory alloys are different from each other when the compositions of the shape memory alloys are different from each other. When current A1 flows through a shape memory alloy with composition 1, heat of the deformation starting temperature T1 is produced so that the shape memory alloy with composition 1 starts its deformation. At this stage, the shape memory alloy with composition 2 does not start its deformation yet because the temperature does not reach the deformation starting temperature T2 (>T1) yet. When current A2 (>A1) flows through the shape memory alloys with composition 2, this shape memory alloy also starts its deformation because the temperature reaches the deformation starting temperature T2. At this stage, the shape memory alloy with composition 1 already starts its deformation. Similar effects can be obtained by change the shape memory temperature without changing the composition of alloys. Therefore, it is also preferable to change the shape memory temperature and make use of such a effect.

Figure 78:
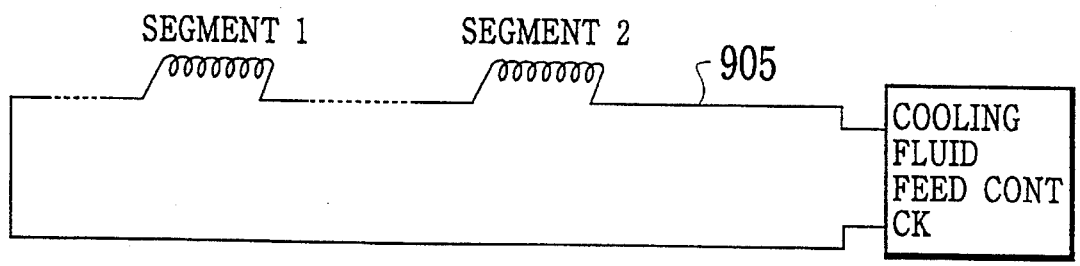
FIG. 78 is an illustration showing another example in which a flexible pipe with the shape memory alloys of FIG. 77 are divided into several segments.

The example shown in FIG. 78 makes use of the above way, in which the tubular-shaped shape memory alloy 905 shown in FIGS. 72 and 73 is mounted in the outer cover. Segment 1 is made of the shape memory alloy with the component 1 and segment 2 is made of the shape memory alloy with component 2. In this example, when current A1 flows through shape memory alloy 905, only segment 1 is controlled on its flexibility as described above. When current A2 flows through shape memory alloy 905, both of segment i and segment 2 are controlled on their flexibility as described above. Consequently, by changing current supplied to the shape memory alloy 905, it is possible to control each segment separately or to control a plurality of segments simultaneously. By using this example, it is possible to unify or simplify the path of the cooling fluid and the wiring and the structure of the flexible pipe so that it becomes possible to make the flexible pipe slim and to simplify the manufacturing process. Though the explanation is made about the example with two segments, the number of the segments and the composition of the shape memory alloy in each segment may be optionally selected.

In the above-mentioned embodiments, since the operator can control the flexibility of the flexible pipe for each segment so that the flexibility of the endoscope can be increased apparently when the endoscope is inserted for diagnosis, it is possible to insert the endoscope smoothly without causing pain to the patient, thus reducing the diagnosis time.

What is claimed is:

1. An endoscope system comprising:

an endoscope section having a flexible pipe insertable into a body cavity, said flexible pipe including a plurality of segments with flexibility variation means for varying the flexibility of each of said segments;

a monitor section for displaying images obtained by said endoscope as a picture; and a main frame unit having a flexibility control section for controlling the flexibility of said flexibility variation means for each segment and an image display control section for controlling said monitor section; wherein said main frame unit further comprises a central control section for controlling said flexibility control section and said image display control section, a data base for storing flexibility quantities for each segment of said flexible pipe in the form of a plurality of flexibility control patterns, and input means for inputting data to said central control section, said monitor section includes a display for displaying at least one flexibility control pattern as a picture, said central control section extracts any flexibility control patterns from said data base on the basis of data inputted by said input means to said central control section and further displays extracted patterns on said display, and when any one of said displayed flexibility control patterns is selected by said input means, said flexibility control section controls the flexibility of said flexibility variation means in accordance with said selected flexibility control pattern.

2. The endoscope system of claim 1, wherein said data base includes learning means for learning a new flexibility control pattern obtained according to a diagnosis situation.

3. The endoscope system of claim 1, wherein said flexible pipe is formed with a shape memory alloy as said flexibility variation means, and the flexibility of said flexible pipe is controlled by passing current through said shape memory alloy from said flexibility control section to change a hardness thereof.

4. The endoscope system of claim 3, wherein said shape memory alloy is of a helical form.

5. The endoscope system of claim 2, further comprising:

an X-ray fluoroscopic apparatus for fluoroscopically observing said body cavity into which said flexible pipe is insertable; and designating means for designating a flexibility quantity of each segment;

and wherein said monitor section includes a display for displaying flexibility quantities for each segment of said flexible pipe in the form of a plurality of flexibility control patterns, and when a flexibility quantity of each segment is designated by said designating means, said flexibility control section controls the flexibility of said flexibility variation means in accordance with a designated flexibility control pattern.

6. An endoscope system comprising:

an endoscope section having a flexible pipe insertable into a body cavity, said flexible pipe including a plurality of segments with flexibility variation means for varying the flexibility of each of said segments;

a monitor section for displaying images obtained by said endoscope as a picture; and a main frame unit having a flexibility control section for controlling the flexibility of said flexibility variation means for each segment and an image display control section for controlling said monitor section;

wherein said flexible pipe is formed with a shape memory alloy as said flexibility variation means, and the flexibility of said flexible pipe is controlled by passing current through said shape memory alloy from said flexibility control section to change a hardness thereof, and wherein said shape memory alloy is formed as a wave-shaped spring.

7. The endoscope system of claim 6, wherein said shape memory alloy is formed into a tubular shape so that cooling water can be fed therethrough.

* * * * *